United States Patent
Sing et al.

(10) Patent No.: US 11,452,824 B2
(45) Date of Patent: Sep. 27, 2022

(54) RESPIRATORY THERAPY FILTER, FLOW CONTROL, AND PATIENT INTERFACE APPARATUSES, SYSTEMS, AND METHODS

(71) Applicant: Hill-Rom Services PTE. LTD., Singapore (SG)

(72) Inventors: Jack B. Sing, Batesville, IN (US); Nookarajesh Varma Sangadi, Singapore (SG); Michael M. Frondorf, Lakeside Park, KY (US); Pratheep K. Mahalingam, Singapore (SG); Suresha Venkataraya, Singapore (SG); Yue Wang, Singapore (SG); Chau Chong Ye, Singapore (SG); Joel Preetham Fernandes, Singapore (SG); Cong Jiang, Singapore (SG); Wei T. Tan, Singapore (SG); Eugene Kung, Singapore (SG); Siew Ying Koh, Singapore (SG); Tak Wei David Teo, Singapore (SG); Leah Noaeill, New Brighton, MN (US)

(73) Assignee: Hill-Rom Services PTE. LTD., Singapore (SG)

( * ) Notice: Subject to any disclaimer, the term of this patent is extended or adjusted under 35 U.S.C. 154(b) by 488 days.

(21) Appl. No.: 15/901,114

(22) Filed: Feb. 21, 2018

(65) Prior Publication Data
US 2018/0243518 A1    Aug. 30, 2018

Related U.S. Application Data

(60) Provisional application No. 62/463,806, filed on Feb. 27, 2017.

(51) Int. Cl.
*A61M 11/02* (2006.01)
*A61M 16/06* (2006.01)
(Continued)

(52) U.S. Cl.
CPC ........ *A61M 11/02* (2013.01); *A61M 16/0006* (2014.02); *A61M 16/024* (2017.08);
(Continued)

(58) Field of Classification Search
CPC .............. A61M 16/00; A61M 16/0006; A61M 16/0605; A61M 16/08; A61M 16/0808;
(Continued)

(56) References Cited

U.S. PATENT DOCUMENTS

| | | | |
|---|---|---|---|
| 4,852,563 A * | 8/1989 | Gross | A61M 16/08 128/202.27 |
| 6,550,476 B1 | 4/2003 | Ryder | |

(Continued)

FOREIGN PATENT DOCUMENTS

| | | |
|---|---|---|
| WO | 2006102345 A2 | 9/2006 |
| WO | 2009042187 A1 | 4/2009 |

(Continued)

OTHER PUBLICATIONS

Examination report No. 2 for standard patent application for Australian Patent Application No. 2018201332 dated Dec. 4, 2018; 4 pages.

(Continued)

*Primary Examiner* — Elliot S Ruddie
(74) *Attorney, Agent, or Firm* — Barnes & Thornburg LLP

(57) ABSTRACT

A nebulizer assembly for a respiratory device is provided having a housing defining a chamber. The housing also has a nebulizer port configured to receive a nebulizer to discharge atomized medication into the chamber. An outlet of a handle is coupled to the inlet of the housing. A hose is coupled to an inlet of the handle. A patient interface is coupled to the outlet of the housing. Air flows from the hose (Continued)

to the patient interface via the handle and the housing. The air mixes with the atomized medication within the chamber.

18 Claims, 38 Drawing Sheets

(51) Int. Cl.

| | |
|---|---|
| *A61M 16/20* | (2006.01) |
| *A61M 16/00* | (2006.01) |
| *A61M 16/10* | (2006.01) |
| *A61M 16/08* | (2006.01) |
| *A61M 16/14* | (2006.01) |
| *A61M 11/06* | (2006.01) |
| *A61M 15/00* | (2006.01) |
| *A61M 16/04* | (2006.01) |
| *A61M 11/00* | (2006.01) |

(52) U.S. Cl.
CPC .... *A61M 16/0605* (2014.02); *A61M 16/0683* (2013.01); *A61M 16/0816* (2013.01); *A61M 16/0833* (2014.02); *A61M 16/0858* (2014.02); *A61M 16/106* (2014.02); *A61M 16/1055* (2013.01); *A61M 16/14* (2013.01); *A61M 16/202* (2014.02); *A61M 11/00* (2013.01); *A61M 11/005* (2013.01); *A61M 11/06* (2013.01); *A61M 15/0085* (2013.01); *A61M 16/0009* (2014.02); *A61M 16/0066* (2013.01); *A61M 16/0488* (2013.01); *A61M 16/06* (2013.01); *A61M 16/1005* (2014.02); *A61M 2016/0027* (2013.01); *A61M 2016/0036* (2013.01); *A61M 2202/0208* (2013.01); *A61M 2205/14* (2013.01); *A61M 2205/502* (2013.01); *A61M 2205/52* (2013.01); *A61M 2205/75* (2013.01); *A61M 2205/7581* (2013.01); *A61M 2205/8206* (2013.01); *A61M 2206/11* (2013.01); *A61M 2206/16* (2013.01); *A61M 2209/08* (2013.01); *A61M 2230/20* (2013.01)

(58) Field of Classification Search
CPC .......... A61M 16/0816; A61M 16/0833; A61M 16/0858; A61M 16/106; A61M 16/202; A61M 16/024; A61M 16/0683; A61M 16/1055; A61M 16/14; A61M 16/0009; A61M 16/1005; A61M 16/0066; A61M 16/0488; A61M 16/06; A61M 2016/0027; A61M 2016/0036; A61M 2202/0208; A61M 2205/14; A61M 2205/502; A61M 2205/52; A61M 2205/75; A61M 2205/7581; A61M 2205/8206; A61M 2206/11; A61M 2206/16; A61M 2209/08; A61M 2230/20; A61M 11/00; A61M 11/02; A61M 11/005; A61M 11/006; A61M 11/06; A61M 15/0085; B65D 83/14; B65D 83/16
USPC ....................................... 128/200.14, 200.23
See application file for complete search history.

(56) References Cited

U.S. PATENT DOCUMENTS

| | | | | |
|---|---|---|---|---|
| 6,708,688 | B1 | 3/2004 | Rubin et al. | |
| 6,718,969 | B1 | 4/2004 | Rubin et al. | |
| 6,792,946 | B1 | 9/2004 | Waldo, Jr. et al. | |
| 7,191,780 | B2 | 3/2007 | Faram | |
| 7,909,033 | B2 | 3/2011 | Faram | |
| 8,051,854 | B2 | 11/2011 | Faram | |
| 8,365,727 | B2 | 2/2013 | Dunsmore et al. | |
| 8,485,179 | B1 | 7/2013 | Meyer et al. | |
| 8,539,952 | B2 | 9/2013 | Carbone et al. | |
| 8,573,203 | B2 | 11/2013 | Addington et al. | |
| 8,931,478 | B2 | 1/2015 | Dunsmore et al. | |
| 9,050,434 | B2 | 6/2015 | Faram | |
| 9,272,115 | B2 | 3/2016 | Bobey et al. | |
| 9,675,775 | B2 | 6/2017 | Bobey et al. | |
| 9,757,528 | B2 | 9/2017 | Rubin | |
| 2005/0217666 | A1* | 10/2005 | Fink | A61M 16/0858 128/200.14 |
| 2011/0146670 | A1 | 6/2011 | Gallem et al. | |
| 2016/0106947 | A1* | 4/2016 | Flynn | A61M 16/14 128/200.14 |
| 2017/0007797 | A1 | 1/2017 | Islava | |
| 2018/0085541 | A1* | 3/2018 | Ye | A61M 16/0009 |

FOREIGN PATENT DOCUMENTS

| | | | |
|---|---|---|---|
| WO | 2014120024 | A1 | 8/2014 |
| WO | 2016159889 | A1 | 10/2016 |

OTHER PUBLICATIONS

Australian Examination Report No. 1 for Application No. 2019208231, dated Oct. 2, 2019, 4 pages.
EP Search Report for European Patent Application No. 18158684.3 dated Jun. 6, 2018; 10 pages.
Australian Examination Report No. 1 for Standard Patent Application in Australian Patent Application No. 2018201332 dated Aug. 25, 2018; 5 pages.
Australian Examination Report No. 2 for Application No. 2020205354, dated Feb. 4, 2022, 5 pages.

* cited by examiner

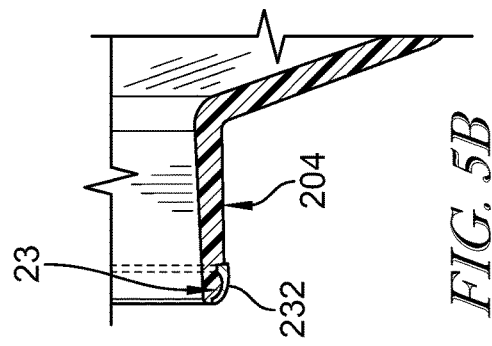
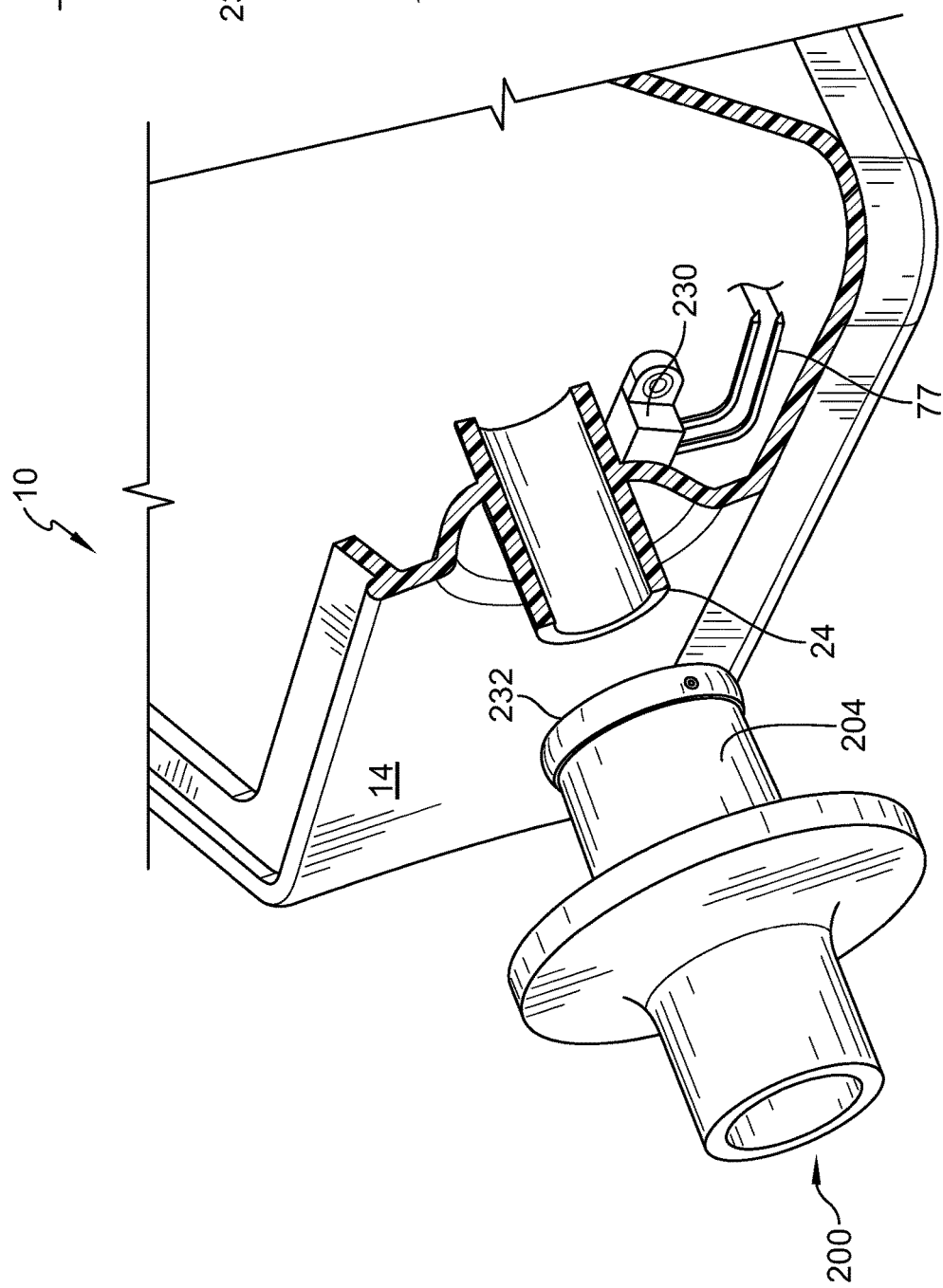

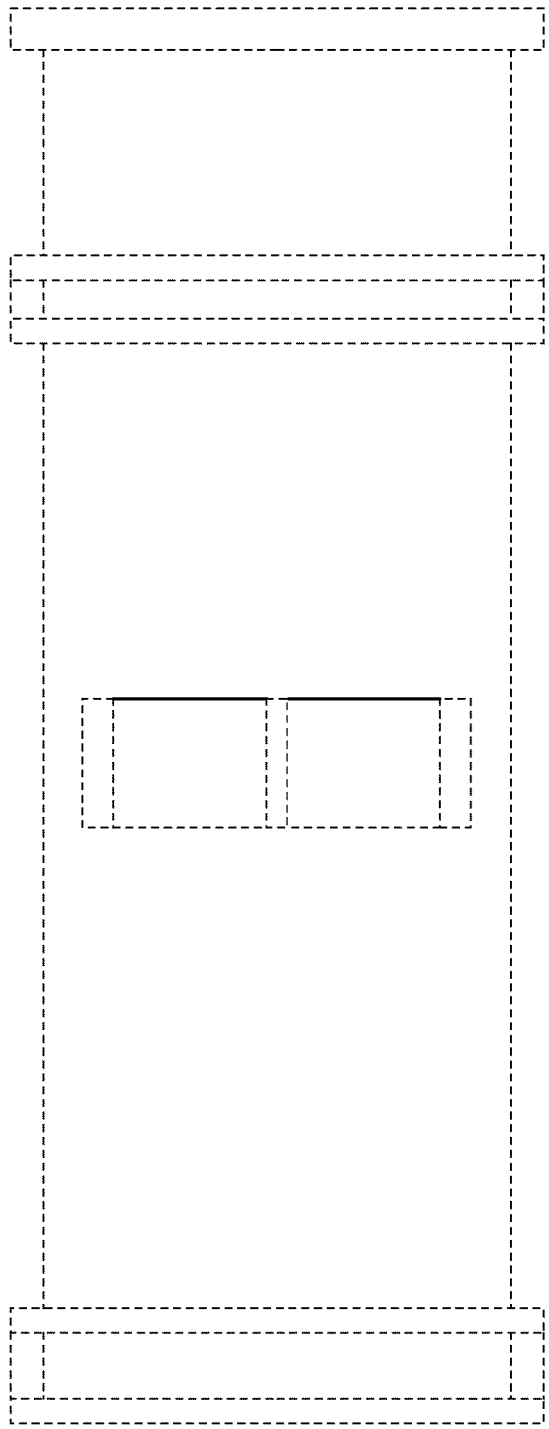 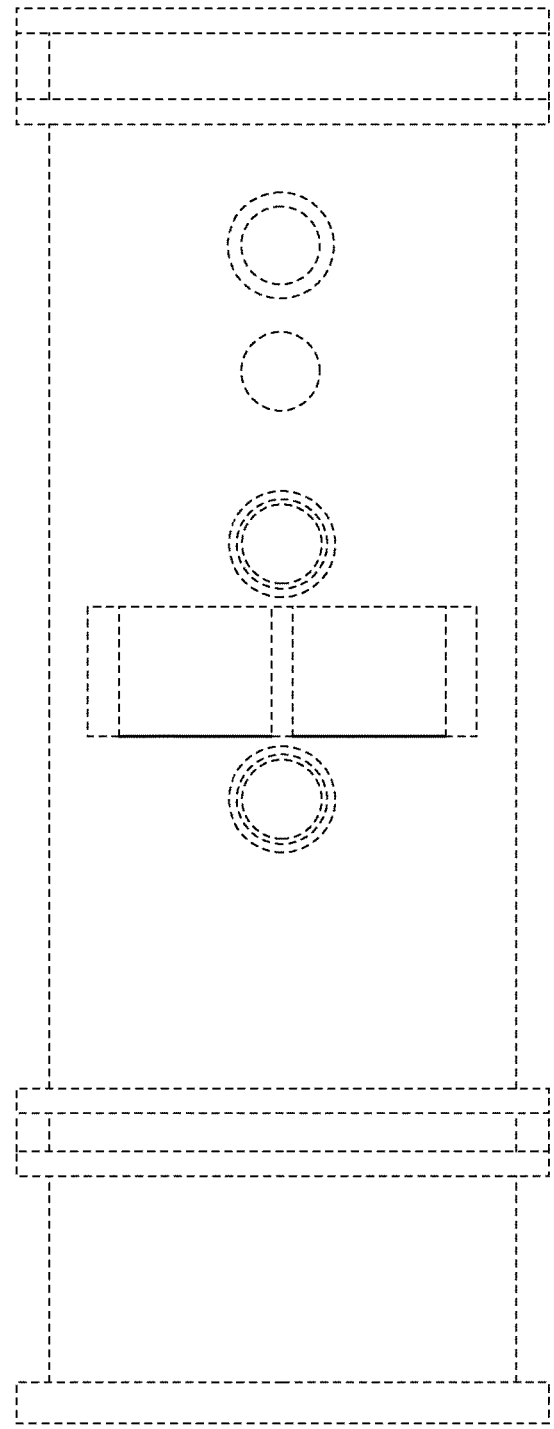
FIG. 43                    FIG. 44

RESPIRATORY THERAPY FILTER, FLOW CONTROL, AND PATIENT INTERFACE APPARATUSES, SYSTEMS, AND METHODS

CROSS-REFERENCE TO RELATED APPLICATIONS

This application claims priority under 35 U.S.C. § 119 to U.S. Patent App. Ser. No. 62/463,806 entitled "RESPIRATORY THERAPY FILTER, FLOW CONTROL, AND PATIENT INTERFACE APPARATUSES, SYSTEMS, AND METHODS," which was filed Feb. 27, 2017 and is expressly incorporated herein by reference.

BACKGROUND

The present disclosure relates to respiratory devices and particularly, to respiratory devices that are operable to apply varying levels of oscillating pressure to an airway of a patient.

Respiratory devices that provide positive pressure to a person's airway are known. For example, there are Continuous Positive Airway Pressure (CPAP) devices that apply positive pressure to a person's airway at a substantially constant level during the person's inhalation and exhalation. There are also Bi-Level CPAP devices that apply varying levels of positive pressure to a person, such as applying a first amount of positive pressure during inhalation and a second amount of positive pressure during exhalation.

Respiratory devices that provide negative pressure or suction to a person's airway are also known. One category of such devices is mechanical insufflation/exsufflation (MIE) devices. These devices are sometimes referred to as cough assist devices. This is because application of positive pressure followed by application of negative pressure to a person's airway simulates a cough and assists the person in expelling mucus from their airway. One such known cough assist device is the VITALCOUGH™ System available from Hill-Rom Company, Inc. In this regard, see U.S. Pat. No. 8,539,952 which is hereby incorporated by reference herein.

Respiratory devices that are capable of applying both positive and negative pressure to a person's airway sometimes have a pressure source, such as a blower, and at least one valve that changes position to selectively connect either the outlet of the blower or the inlet of the blower to a patient interface, such as a mask or mouthpiece and related tubing, to apply the positive pressure or the negative pressure, respectively, to the person's airway. Other respiratory devices have separate positive pressure and negative pressure sources.

Some respiratory devices include additional structural elements, such as one or more valves, diaphragm pumps, acoustic devices, or piezoelectric devices that operate to provide oscillations in the baseline pressure levels being applied to the person's airway. These additional structural elements to produce the oscillations add cost, size and weight to the respiratory device. Patients and caregivers, therefore, may appreciate respiratory devices capable of producing oscillatory pressures, such as positive pressures or negative pressures or both, but that are smaller, less expensive, and lighter in weight than known respiratory devices.

SUMMARY

The present disclosure includes one or more of the features recited in the appended claims and/or the following features which, alone or in any combination, may comprise patentable subject matter.

According to a first aspect of the disclosure, a respiratory device includes a housing having a hose port. A magnetic proximity switch is positioned within the housing adjacent to the hose port. A filter is sized to be positioned on the hose port. The filter has a filtration chamber positioned between a filter inlet and a filter outlet. A metal end piece is coupled to the inlet of the filter.

In some embodiments, the metal end piece activates the magnetic proximity switch when the filter inlet is coupled to the hose port. In some embodiments, the device includes an indicator that is activated when the magnetic proximity switch is activated. In some embodiments, the indicator includes a display on the housing. An icon is displayed on the display when the magnetic proximity switch is activated. In some embodiments, the indicator includes an audible indicator within the housing. The audible indicator provides an audible notification when the magnetic proximity switch is activated. In some embodiments, the indicator is activated when the magnetic proximity switch is not activated. In some embodiments, an icon is displayed on the display when the magnetic proximity switch is not activated. In some embodiments, the audible indicator provides an audible notification when the magnetic proximity switch is not activated.

In some embodiments, the metal end piece is positioned around a perimeter of the filter inlet. In some embodiments, the filter inlet is positionable on the hose port in different rotational positions. In some embodiments, the housing includes a body. The hose port extends from the body. The magnetic proximity switch is coupled to the body of the housing adjacent to the hose port. In some embodiments, the body includes an inner sidewall and an opposite outer sidewall. The magnetic proximity switch is coupled to the inner sidewall.

According to a second aspect of the disclosure, a method of verifying that a filter is coupled to a respiratory device includes coupling a magnetic proximity switch within a housing adjacent to a hose port. The method also includes coupling a metal end piece to a filter inlet of a filter, wherein the metal end piece activates the magnetic proximity switch when the filter inlet is coupled to the hose port.

In some embodiments, the filter inlet is positionable on the hose port in different rotational positions. In some embodiments, the method includes activating an indicator when the magnetic proximity switch is activated. In some embodiments, activating the indicator includes displaying an icon on a display of the housing. In some embodiments, activating the indicator includes activating an audible notification. In some embodiments, the method includes activating the indicator when the magnetic proximity switch is not activated.

In some embodiments, the method includes positioning the metal end piece around a perimeter of the filter inlet. In some embodiments, the method includes positioning the filter inlet on the hose port in different rotational positions. In some embodiments, the method includes coupling the magnetic proximity switch to a body of the housing adjacent to the hose port. In some embodiments, the method includes coupling the magnetic proximity switch to an inner sidewall of the body.

According to a third aspect of the disclosure, a respiratory device includes a housing having a hose port. A switch is positioned within the housing. A rotatable arm is positioned adjacent to the hose port. The rotatable arm is configured to activate the switch. A filter is sized to be positioned on the hose port. The filter has a filtration chamber positioned between a filter inlet and a filter outlet. When the filter is positioned on the hose port the filter inlet engages the rotatable arm to activate the switch.

In some embodiments, when the filter is positioned on the hose port the rotatable arm rotates toward the switch to activate the switch. In some embodiments, the switch includes a lever. The rotatable arm engages the lever when the rotatable arm rotates toward the switch. In some embodiments, the device includes an indicator. The indicator is activated when the switch is activated. In some embodiments, the indicator includes a display on the housing. An icon is displayed on the display when the magnetic proximity switch is activated. In some embodiments, the indicator includes an audible indicator within the housing. The audible indicator provides an audible notification when the magnetic proximity switch is activated. In some embodiments, the indicator activated when the switch is not activated. In some embodiments, an icon is displayed on the display when the magnetic proximity switch is not activated. In some embodiments, the audible indicator provides an audible notification when the magnetic proximity switch is not activated.

According to a fourth aspect of the disclosure, a method of verifying that a filter is coupled to a respiratory device includes coupling a switch within a housing having a hose port. The method also includes positioning a rotatable arm adjacent to the hose port, wherein when a filter is positioned on the hose port a filter inlet engages the rotatable arm so that the rotatable arm rotates toward the switch to activate the switch.

In some embodiments, the method also includes activating an indicator when the switch is activated. In some embodiments, activating the indicator includes displaying an icon on a display of the housing. In some embodiments, activating the indicator includes activating an audible notification. In some embodiments, the method includes activating the indicator when the switch is not activated.

According to a fifth aspect of the disclosure, a respiratory device includes a housing having a hose port. A control circuitry is positioned within the housing. A blower is positioned within the housing. The blower has a blower inlet and a blower outlet. The blower outlet is in flow communication with the hose port. A filter is sized to be positioned on the outlet of the housing. The filter has a filtration chamber positioned between a filter inlet and a filter outlet. The blower is operable to generate airflow through the filter. The control circuitry detects a pressure and a flowrate of the airflow through the filter to determine whether the filter needs to be replaced.

In some embodiments, the control circuitry determines whether the filter needs to be replaced based on a ratio of the flowrate to the pressure of airflow through the filter. In some embodiments, the control circuitry compares the ratio to a threshold ratio to determine whether the filter needs to be replaced. In some embodiments, the control circuitry compares a detected pressure to a threshold pressure to determine whether the filter needs to be replaced. In some embodiments, the control circuitry compares a detected flowrate to a threshold flowrate to determine whether the filter needs to be replaced. In some embodiments, the device includes an indicator, the indicator indicating whether the filter needs to be replaced. In some embodiments, the indicator includes a display on the housing, an icon displayed on the display when the filter needs to be replaced. In some embodiments, the indicator includes a display on the housing, an icon displayed on the display when the filter does not need to be replaced. In some embodiments, the indicator includes an audible indicator within the housing, the audible indicator providing an audible notification when the filter needs to be replaced. In some embodiments, the indicator includes an audible indicator within the housing, the audible indicator providing an audible notification when the filter does not need to be replaced.

According to a sixth aspect of the disclosure, a method for determining when a filter for a respiratory device needs to be replaced includes generating airflow through the filter with a blower positioned within a housing of the respiratory device. The method also includes detecting a pressure and a flowrate of the airflow through the filter. The method also includes comparing the pressure and the flowrate of the airflow through the filter to threshold pressure and flowrate values to determine whether the filter needs to be replaced.

In some embodiments, the method includes determining a ratio of the pressure to the flowrate of airflow through the filter to determine whether the filter needs to be replaced. In some embodiments, the method includes comparing the ratio to a threshold ratio to determine whether the filter needs to be replaced. In some embodiments, the method includes comparing a detected pressure to a threshold pressure to determine whether the filter needs to be replaced. In some embodiments, the method includes comparing a detected flowrate to a threshold flowrate to determine whether the filter needs to be replaced. In some embodiments, the method includes providing a notification indicating whether the filter needs to be replaced. In some embodiments, the method includes displaying an icon on a display indicating that the filter needs to be replaced. In some embodiments, the method includes displaying an icon on a display indicating that the filter does not need to be replaced. In some embodiments, the method includes providing an audible notification indicating that the filter needs to be replaced. In some embodiments, the method includes providing an audible notification indicating that the filter does not need to be replaced.

According to a seventh aspect of the disclosure, a respiratory device includes a housing having a hose port. A tag reader is positioned in proximity to the hose port. A filter is sized to be positioned on the hose port of the housing. The filter has a filtration chamber positioned between a filter inlet and a filter outlet. An identification tag is coupled to the filter. The tag reader reads the tag to identify the filter when the filter is coupled to the hose port.

In some embodiments, the identification tag is a radio-frequency identification tag and the tag reader is a radio frequency identification tag reader. In some embodiments, the identification tag communicates with the tag reader through near field communication. In some embodiments, control circuitry is positioned within the housing and electronically coupled to the tag reader. The control circuitry includes a memory. In some embodiments, the control circuitry tracks a usage of the filter with the respiratory device. The memory stores a number indicating the usage of the filter. In some embodiments, the usage of the filter includes the number of times that the filter has been used with the respiratory device. In some embodiments, the usage of the filter includes the overall time that the filter has been used with the respiratory device. In some embodiments, the control circuitry compares the usage of the filter with the respiratory device to a threshold number.

In some embodiments, the filter is a first filter. The respiratory device includes a second filter. The control circuitry tracks the usage of the first filter with the respiratory device and a usage of the second filter with the respiratory device. In some embodiments, the usage of the first filter with the respiratory device is different than the usage of the second filter with the respiratory device. In some embodiments, the identification tag is a first identification tag coupled to the first filter and the second filter includes a second identification tag. The tag reader identifies the first filter when the first identification tag is read upon coupling the first filter to the hose port. The tag reader identifies the second filter when the second identification tag is read upon coupling the second filter to the hose port. In some embodiments, the device includes a display. The number indicating the usage of the first filter with the respiratory device is displayed on the display when the first filter is coupled to the hose port. A number indicating the usage of the second filter with the respiratory device is displayed on the display when the second filter is coupled to the hose port.

In some embodiments, the device includes a display to display the number indicating the usage of the filter with the respiratory device. In some embodiments, if the usage of the filter with the respiratory device exceeds a predetermined threshold a notification is provided. In some embodiments, the notification indicates that the filter needs to be replaced after a number of times that the filter has been used exceeds 90. In some embodiments, the notification includes an icon displayed on the display. In some embodiments, the device includes an alarm. The notification includes triggering the alarm.

According to an eighth aspect of the disclosure, a method for determining when a filter for a respiratory device needs to be replaced includes positioning a filter on a hose port of a housing of a respiratory device. The filter has an identification tag. The method also includes reading the identification tag with a tag reader positioned in proximity to the outlet. The method also includes tracking a usage the filter with the respiratory device. The method also includes storing a number indicating the usage of the filter in a memory of the respiratory device.

In some embodiments, tracking a usage of the filter includes tracking a number of times that the filter has been used with the respiratory device. In some embodiments, tracking a usage of the filter includes tracking an overall time that the filter has been used with the respiratory device. In some embodiments, the identification tag is a radio-frequency identification tag and the tag reader is a radio frequency identification tag reader. The method includes reading the radio-frequency identification tag with the radio frequency identification tag reader. In some embodiments, the method also includes communicating between the identification tag and the tag reader through near field communication. In some embodiments, the method also includes displaying on a display the number indicating the usage of the filter with the respiratory device. In some embodiments, the method also includes providing a notification if the usage of the filter exceeds a predetermined threshold. In some embodiments, the method also includes providing the notification on the display. In some embodiments, the method also includes providing the notification through an alarm. In some embodiments, the method also includes indicating that the filter needs to be replaced after a number of times that the filter has been used exceeds 90.

In some embodiments, the filter is a first filter. The method also includes tracking a usage of the first filter with the respiratory device; and tracking a usage of a second filter with the respiratory device. In some embodiments, the identification tag is a first identification tag. The method also includes identifying the first filter when a first identification tag of the first filter is read upon coupling the first filter to the hose port. The method also includes identifying the second filter when a second identification tag of the second filter is read upon coupling the second filter to the hose port. In some embodiments, the method also includes displaying the number indicating the usage of the first filter on a display when the first filter is coupled to the hose port. In some embodiments, the method also includes displaying a number indicating the usage of the second filter on the display when the second filter is coupled to the hose port.

According to a ninth aspect of the disclosure, a respiratory device includes a housing having a hose port. A blower is positioned within the housing. The blower has a blower inlet and a blower outlet. The blower outlet is in flow communication with the hose port. A laminar flow structure is positioned between the blower outlet and the hose port. The laminar flow structure is configured to convert airflow discharged from the blower outlet into a laminar airflow. A control circuitry is configured to measure a pressure drop of the laminar airflow through the laminar flow structure.

In some embodiments, the laminar flow structure includes a vent positioned between an inlet and an outlet of the laminar flow structure. The vent is configured to generate the laminar airflow. In some embodiments, the vent includes a central ring defining an aperture and having at least one spoke extending radially outwardly therefrom. In some embodiments, the vent includes at least one vane extending circumferentially about the central ring from the at least one spoke. In some embodiments, the vent includes a plurality of spokes. A plurality of vanes extends circumferentially about the central ring between each of the plurality of spokes. A first of the plurality of vanes is positioned radially inwardly from a second of the plurality of vanes.

In some embodiments, the laminar flow structure includes a first sensor outlet and a second sensor outlet. The first sensor outlet is positioned upstream of the vent and the second sensor outlet is positioned downstream of the vent. In some embodiments, the first sensor outlet is positioned between the vent and the inlet of the laminar flow structure, and the second sensor outlet is positioned between the vent and the outlet of the laminar flow structure. In some embodiments, the first sensor outlet and the second sensor outlet are each in flow communication with a pressure sensor and a flowrate sensor. The control circuitry measures the pressure and flowrate of the laminar airflow at each of the first sensor outlet and the second sensor outlet to determine a pressure drop of the laminar airflow. In some embodiments, the first sensor outlet and the second sensor outlet are aligned about a line extending parallel to an axis of the laminar flow structure. In some embodiments, the first sensor outlet and the second sensor outlet are misaligned with respect to a line extending parallel to an axis of the laminar flow structure. In some embodiments, the laminar flow structure includes a plurality of first sensor outlets. In some embodiments, the laminar flow structure includes a plurality of second sensor outlets.

In some embodiments, the laminar airflow through the laminar flow structure has a maximum pressure of approximately 80 $cmH_2O$ when the flowrate is between approximately 160 and approximately 180 liters per minute. In some embodiments, the laminar airflow through the laminar flow structure has a maximum pressure of approximately 80 $cmH_2O$ when the flowrate is between approximately 170 and approximately 190 liters per minute. In some embodiments, the laminar airflow through the laminar flow structure has a maximum pressure of approximately 80 $cmH_2O$ when the flowrate is between approximately 160 and approximately 190 liters per minute.

According to a tenth aspect of the disclosure, a method of measuring airflow through a respiratory device includes discharging airflow from an outlet of a blower positioned within a housing of the respiratory device. The method also includes passing the airflow through a laminar flow structure positioned between the outlet of the blower and a hose port of the housing, wherein the laminar flow structure converts the airflow discharged from the blower into a laminar airflow. The method also includes measuring a pressure drop of the laminar airflow through the laminar flow structure.

In some embodiments, the method includes converting the airflow discharged from the blower into the laminar airflow by passing the airflow discharged from the blower through a vent positioned between an inlet and an outlet of the laminar flow structure. In some embodiments, the method includes passing the airflow discharged from the blower through a vent having a central aperture with at least one spoke extending radially outwardly therefrom.

In some embodiments, the vent includes at least one vane extending circumferentially about the central aperture from the at least one spoke. In some embodiments, the vent includes a plurality of spokes. A plurality of vanes extends circumferentially about the central aperture between each of the plurality of spokes. A first of the plurality of vanes is positioned radially inwardly from a second of the plurality of vanes. In some embodiments, the method includes passing the airflow discharged from the blower past a first sensor outlet and a second sensor outlet, wherein the first sensor outlet is positioned upstream of the vent and the second sensor outlet is positioned downstream of the vent. In some embodiments, the first sensor outlet is positioned between the vent and the inlet of the laminar flow structure, and the second sensor outlet is positioned between the vent and the outlet of the laminar flow structure. In some embodiments, the first sensor outlet and the second sensor outlet are each in flow communication with a pressure sensor and a flowrate sensor. The method also includes measuring the pressure and flowrate of the laminar airflow at each of the first sensor outlet and the second sensor outlet to determine a pressure drop of the laminar airflow. In some embodiments, the first sensor outlet and the second sensor outlet are aligned about a line extending parallel to an axis of the laminar flow structure. In some embodiments, the first sensor outlet and the second sensor outlet are misaligned with respect to a line extending parallel to an axis of the laminar flow structure. In some embodiments, the laminar flow structure includes a plurality of first sensor outlets. In some embodiments, the laminar flow structure includes a plurality of second sensor outlets.

In some embodiments, the method includes converting the airflow discharged from the blower to a laminar airflow having a maximum pressure of approximately 80 $cmH_2O$ when the flowrate is between approximately 160 and approximately 180 liters per minute. In some embodiments, the method includes converting the airflow discharged from the blower to a laminar airflow having a maximum pressure of approximately 80 $cmH_2O$ when the flowrate is between approximately 170 and approximately 190 liters per minute. In some embodiments, the method includes converting the airflow discharged from the blower to a laminar airflow having a maximum pressure of approximately 80 $cmH_2O$ when the flowrate is between approximately 160 and approximately 190 liters per minute.

According to an eleventh aspect of the disclosure, a nebulizer assembly for a respiratory device includes a housing defining a chamber. The housing has an inlet in flow communication with the chamber and an outlet in flow communication with the chamber. The inlet and the outlet are linearly offset. The housing has a nebulizer port configured to receive a nebulizer to discharge atomized medication into the chamber. A hose is coupled to the inlet of the housing. A patient interface is coupled to the outlet of the housing. Air flows from the hose to the patient interface via the housing. The air mixes with the atomized medication within the chamber. The linearly offset inlet and outlet of the housing produce turbulent airflow within the chamber to facilitate mixing the air with the atomized medication.

In some embodiments, the device includes at least one of a jet nebulizer, an ultrasonic wave nebulizer, or a vibrating mesh nebulizer coupled to the nebulizer port. In some embodiments, the patient interface includes at least one of a mask or a mouthpiece. In some embodiments, the patient interface includes an adapter that couples to at least one of a mask or a mouthpiece. In some embodiments, the hose is substantially non-linear to produce turbulent airflow through the hose. In some embodiments, the hose couples to a respiratory device. In some embodiments, the housing includes an outer surface having a finger grip defined therein. In some embodiments, the device includes a nebulizer port cap to seal the nebulizer port when the nebulizer assembly is used without a nebulizer. In some embodiments, the device includes an occlusion ring coupled to the inlet of the chamber, the occlusion ring being rotatable to open and close a side vent hole formed in the inlet of the chamber.

According to a twelfth aspect of the disclosure, a nebulizer assembly for a respiratory device includes a housing defining a chamber. The housing has an inlet in flow communication with the chamber and an outlet in flow communication with the chamber. The housing includes a nebulizer port configured to receive a nebulizer to discharge atomized medication into the chamber. A handle has an inlet and an outlet. The handle is curved between the inlet and the outlet. The outlet is coupled to the inlet of the housing. The housing is circumferentially rotatable about the outlet of the handle to position the nebulizer at different circumferential positions with respect the outlet of the handle. A hose is coupled to the inlet of the handle. A patient interface is coupled to the outlet of the housing. Air flows from the hose to the patient interface via the handle and the housing, the air mixing with the atomized medication within the chamber.

In some embodiments, the handle is substantially banana shaped. In some embodiments, the outlet of the handle has a larger circumference than the inlet of the handle. In some embodiments, the inlet of the housing has a larger circumference than the outlet of the housing. In some embodiments, the housing has a substantially frusto-conical shape. In some embodiments, the device includes at least one of a jet nebulizer, an ultrasonic wave nebulizer, or a vibrating mesh nebulizer coupled to the nebulizer port. In some embodiments, the patient interface includes at least one of a mask or a mouthpiece. In some embodiments, the patient interface includes an adapter that couples to at least one of a mask or a mouthpiece. In some embodiments, the hose is substantially non-linear to produce turbulent airflow through the hose. In some embodiments, the hose couples to a respiratory device. In some embodiments, the device includes a nebulizer port cap to seal the nebulizer port when the nebulizer assembly is used without a nebulizer.

Additional features, which alone or in combination with any other feature(s), such as those listed above and/or those listed in the claims, can comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures in which:

FIG. 5A is a perspective view of another embodiment of the device of FIG. 1 having a magnetic proximity switch, and another embodiment of the filter of FIG. 3 having a metal ring thereon;

FIG. 5B is a detailed view of an inlet port of the filter of FIG. 3.

FIGS. 19-46 are design drawings of the laminar flow structure of FIG. 9 that are intended for use with future continuation design applications.

DETAILED DESCRIPTION

Figure 1:
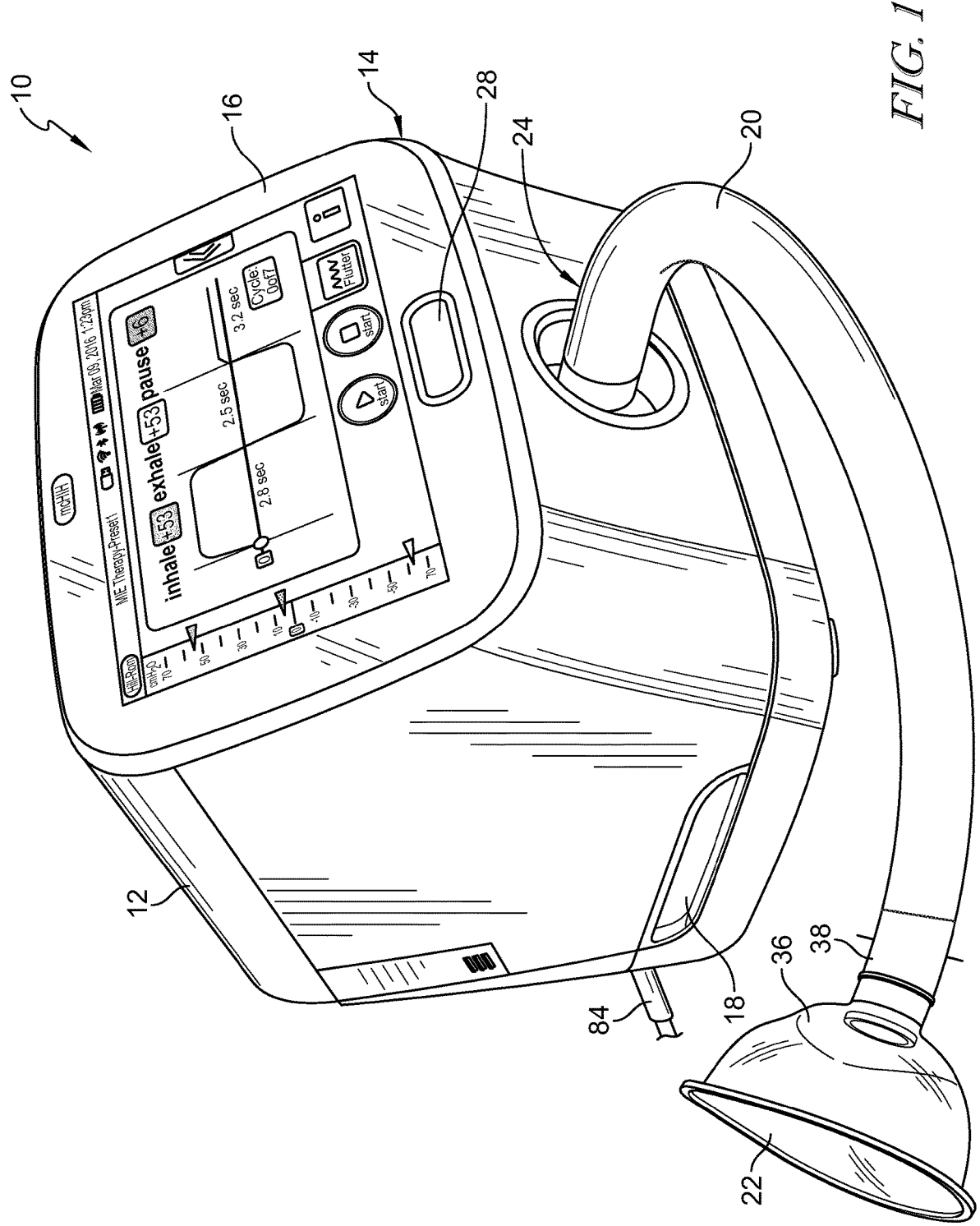
FIG. 1 is a perspective view of a respiratory device having a housing, a patient interface including a hose coupled to the housing at a hose port and a mask at an end of the hose and a graphical user interface (GUI) accessible on a front wall of the housing to control operation of the respiratory device.

A respiratory device 10 is provided. The details of the structure of a suitable respiratory device and related electrical components may be found in International Application No. PCT/SG2016/050166, filed Apr. 1, 2016, published as WO 2016/159889 A1 on Oct. 6, 2016, and titled "Manifold for Respiratory Device," which is hereby incorporated herein in its entirety. Respiratory device 10 includes a housing 12 having a front wall 14 on which a display or graphical user interface 16 is accessible to enter user inputs into device 10 and to view displayed information regarding the operation of device 10 as shown in FIG. 1. Housing 12 is configured with a handle 18 at its bottom which is gripped by a person to carry device 10. At a bottom region of front wall 14 of housing 12, a hose 20 of a patient interface 22 is attached to a hose port 24. Beneath the graphical user interface 16 there is an on/off button 28 that is pressed sequentially to turn device 10 on and off.

Device 10 is operable as an insufflation/exsufflation device or, as such devices are sometimes called, a cough assist device. Thus, device 10 is capable of applying positive pressure and negative pressure to a patient's airway, the positive pressure being applied during insufflation and the negative pressure being applied during exsufflation. The device 10 may be controlled to apply the positive insufflation pressure or the negative insufflation pressure to the patient through the patient interface 22. The user may select to switch between insufflation, exsufflation, and pause pressures. In some embodiments, device 10 is operable to provide other modes of respiratory therapy such as continuous positive expiratory pressure (CPEP) and continuous high frequency oscillation (CHFO), just to name a couple. CPEP and CHFO are sometimes referred to herein, collectively, as Intrapulmonary Percussive Ventilation (IPV).

In the illustrative example, patient interface 22 includes a mask 36 which is configured to engage a patient's face and generally seal the area around the patient's nose and mouth. In other embodiments, patient interface 22 includes a mouthpiece rather than the illustrative mask 36 and the mouthpiece has an end portion that a patient places inside his or her mouth. Patient interface 22 includes a first tubular segment 38 extending from mask 36 and coupled to the hose 20.

Figure 2:
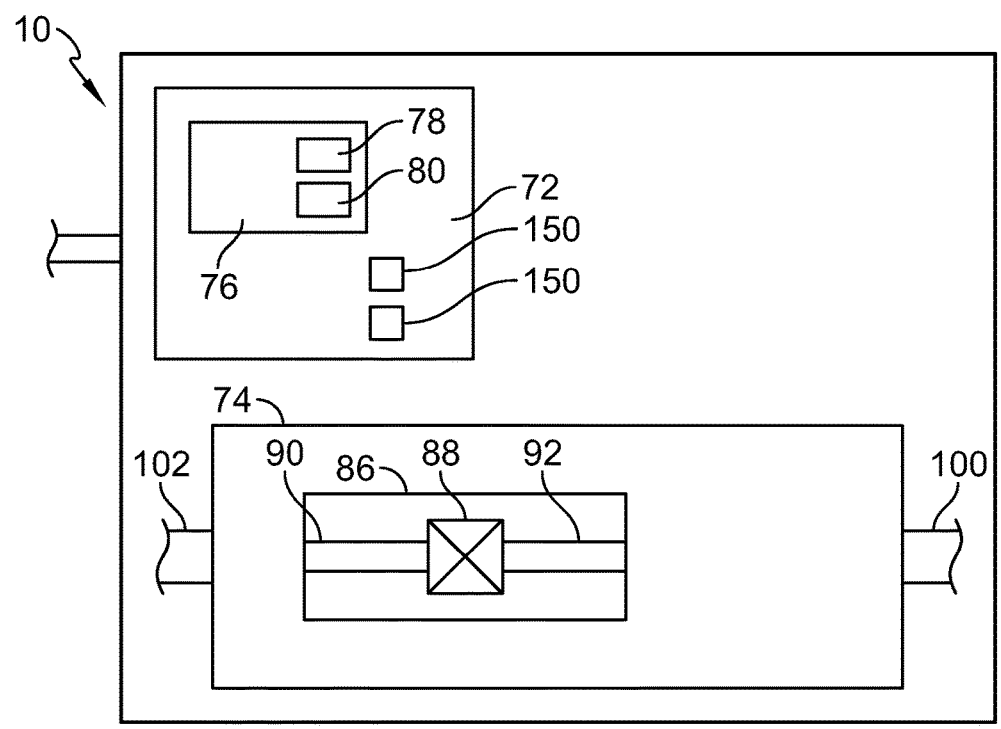
FIG. 2 is a block diagram of internal components of the respiratory device of FIG. 1 showing a pneumatic system and an electrical system.

Referring to FIG. 2, device 10 includes an electrical system 72 (aka control circuitry) and a pneumatic system 74. Electrical system 72 includes control system 76 which, in turn, includes a microprocessor 78 and memory 80. In some embodiments, microprocessor 78 and memory 80 are part of a single microcontroller integrated circuit chip. In some embodiments, GUI 16 and on/off button 28 are electrically coupled to the control system 76. In some embodiments, a foot switch unit, nebulizer, SpO2 port, USB port, and wireless communication module may be coupled electrically to control system 76. An alternating current (AC) power cord may be coupled to control system 76. Control system 76, therefore, includes components to convert the incoming AC power to the proper voltage levels, e.g., 5 Volts (V), 12 V, 24 V, etc., required by various components of device 10. In some embodiments, device 10 includes a lithium ion battery pack which is charged while power cord 84 (shown in FIG. 1) is plugged into a power outlet. In some such embodiments, the components of device 10 are powered from the lithium ion battery pack regardless of whether cord 84 is plugged into a power outlet. Battery packs or batteries that operate according to technologies other than lithium ion technology are also within the scope of this disclosure for use in device 10.

It should be appreciated that although control system 76 is shown diagrammatically as a single block in FIG. 2, it is within the scope of this disclosure for control system 76 of control circuitry 72 to include electrical components that are provided on multiple, separate circuit boards which are interconnected via suitable conductors. It is also within the scope of this disclosure for control system 76 to comprise a single circuit board with the associated electrical components mounted thereon. Of course, some components of electrical system 72 may not be attached to any circuit board at all. For example, buttons and ports may be physically mounted to housing 12 rather than to a circuit board. Ultimately, however, suitable conductors connect these components to control system 76.

Still referring to FIG. 2, pneumatic system 74 includes a blower 86 and a combination direction/oscillation valve 88 pneumatically coupled to an inlet 90 and an outlet 92 of blower 86. In some embodiments, system 74 includes a stepper motor which controls movement of a valve member of valve 88. System 74 includes a conduit 100 that couples valve 88 to patient interface 22 and a conduit 102 that couples valve 88 to atmosphere.

Electrical system 72 includes a plurality of sensors 150 to monitor airflow discharged from the device 10. In some embodiments, at least one sensor 150 monitors a pressure of the airflow discharged from the device 10. In some embodiments, at least one sensor 150 monitors a flowrate of the airflow discharged from the device 10. In some embodiments, sensors 150 may be configured to monitor airflow as it is discharged from the blower 86. In some embodiments, sensors 150 may be configured to monitor airflow as it is flows through any of the conduits described above. In some embodiments, sensors 150 may be configured to monitor airflow as it is flows through the hose port 24. Control system 76 may be configured to operate various algorithms to determine an efficiency of device 10 during operation based on measured pressures and flowrates.

Figure 3:
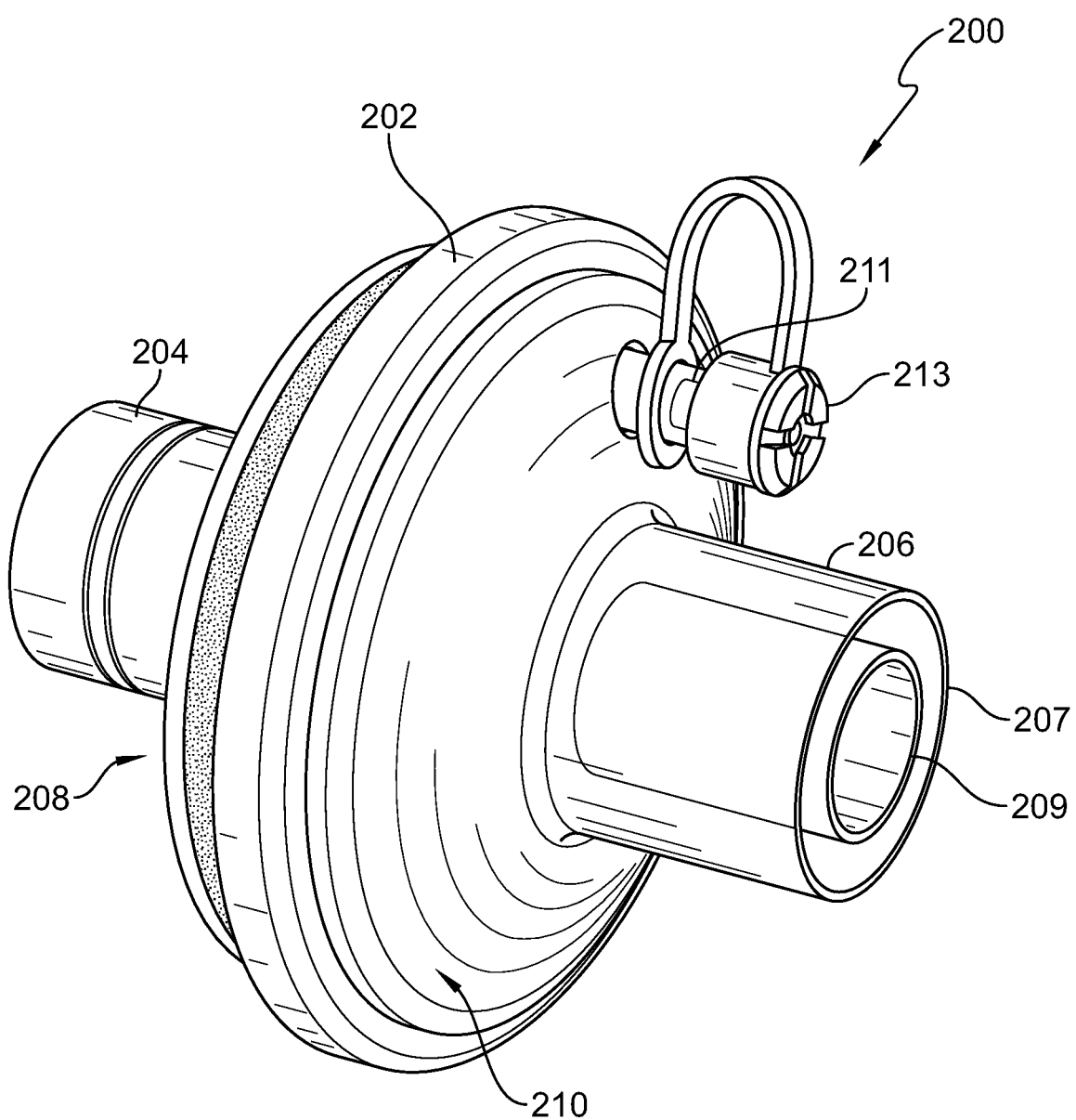
FIG. 3 is a perspective view of an embodiment of a filter that may couple to the hose port of the respiratory device of FIG. 1.

Referring to FIG. 3, a filter 200 is configured to be positioned on the hose port 24. Hose 20 couples to filter 200 so that airflow between device 10 and patient interface 22 passes through filter 200. Filter 200 includes a filtration chamber 202 having a filter inlet 204 and a filter outlet 206. Particularly, filter inlet 204 extends from a first side 208 of filtration chamber 202 and filter outlet 206 extends from a second side 210 of filtration chamber 202. Filtration chamber 202 is substantially cylindrical and has a disk shape. In some embodiments, filtration chamber 202 may take any configuration suitable for housing a filtration element (not shown). The filtration element may be any suitable air filter, viral filter, anti-bacterial filter, or anti-microbial filter, among other things. Filter inlet 204 is substantially cylindrical and extends coaxially with an axis of filtration chamber 202. Filter inlet 204 is sized to be positioned over hose port 24 in a substantially airtight configuration. In some embodiments, any suitable connection between filter inlet 204 and hose port 24 may be made.

Filter outlet 206 is substantially cylindrical and extends coaxially with the axis of filtration chamber 202. Filter outlet 206 is sized so that an end of hose 20 may be positioned thereon in a substantially airtight configuration. In some embodiments, filter outlet 206 includes an outer wall 207 and an inner wall 209 defining a space therebetween. Hose 20 is sized to be positioned within the space defined between outer wall 207 and inner wall 209 in a substantially airtight configuration. In some embodiments, any suitable connection between filter outlet 206 and hose 20 may be made. Filter 200 also includes a valve 211 extending from and in flow communication with filtration chamber 202. The valve 211 may be attached to an oxygen source to supply oxygen to the filtration chamber 202. In one embodiment, the valve 211 may be attached to a source of room air. Valve 211 may include a removable cap 213 thereon to seal the valve 211 when the valve 211 is not in use.

Filter 200 is removable from hose port 24 of device 10 to promote changing filter 200 when filter 200 has become unusable, for example clogged or otherwise incapable of effectively filtering airflow. In some embodiments, control system 76 monitors a pressure and flowrate through filter 200 to determine whether filter 200 needs to be replaced. In such an embodiment, sensors 150 monitor the pressure and flowrate of the air discharged from device 10. The sensors are electrically coupled to control system 76.

Figure 4:
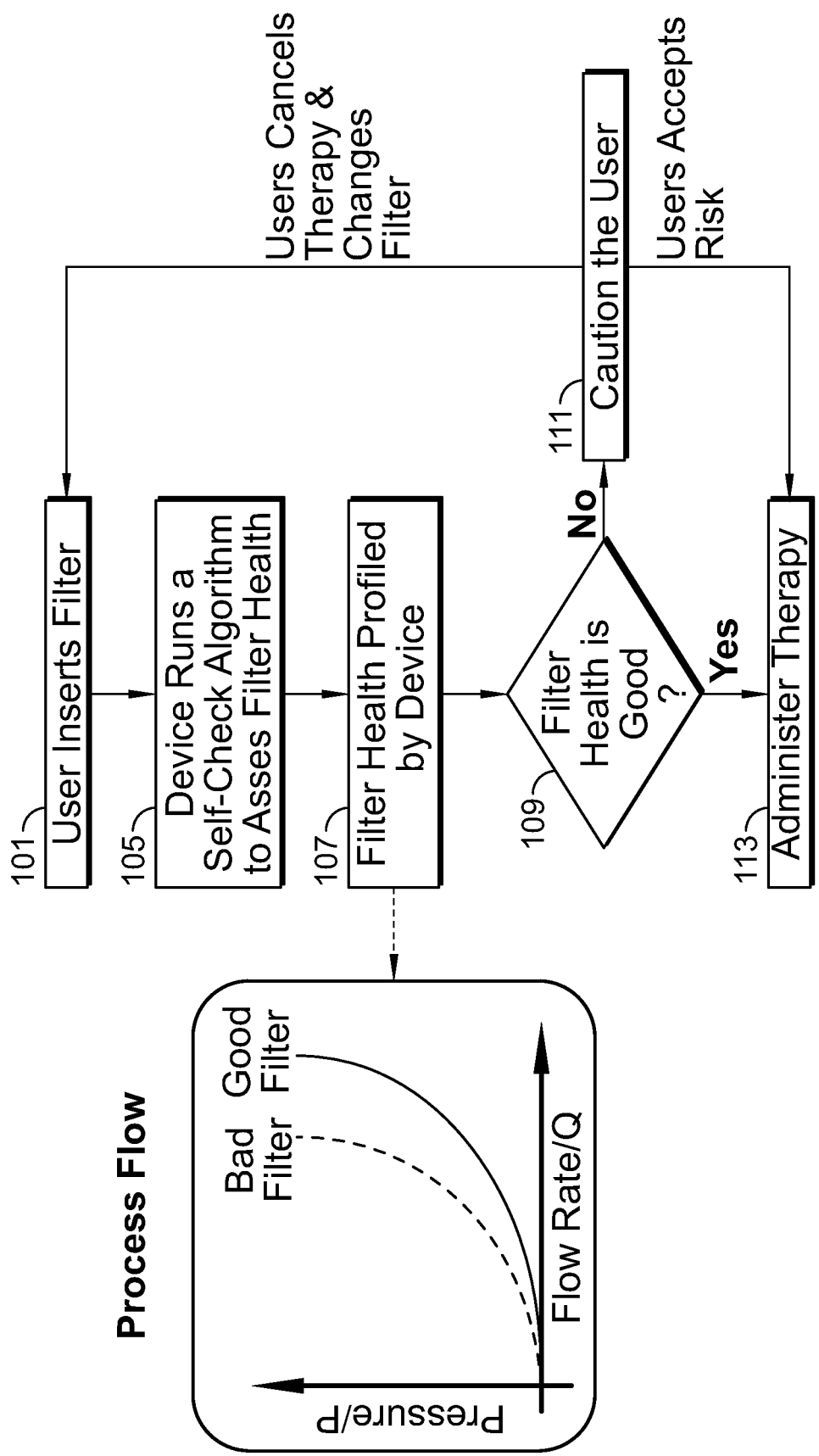
FIG. 4 is a flowchart for assessing a health of the filter of FIG. 3.

Referring to FIG. 4, in some embodiments, prior to use of device 10, a filter 200 is inserted in device 10 by coupling filter 200 to hose port 24 at step 101. Filter 200 is detected by device 10 or, more particularly, by control system 76. Microprocessor 78 of control system 76 runs a self-check algorithm or diagnostic to determine whether device 10 is suitable for use at step 105. The diagnostic may include operating blower 86 to test a flow of air from device 10. In some embodiments, the diagnostic may include testing a flow of air through filter 200 by discharging air into filter 200. The sensors 150 detect the pressure and flowrate of the air being discharged from hose port 24 into filter 200 to determine a filter health profile at step 107. Control system 76 determines a ratio of the flowrate to the pressure. Based on the pressure, the flowrate, the ratio of the flowrate to pressure, or any combination thereof, the control system 76 determines whether filter 200 is blocking airflow from device 10, i.e. is the filter "good" or "bad, at step 109. Particularly, the pressure, the flowrate, the ratio of the flowrate to pressure, or any combination thereof may be indicative of a clogged or overused filter 200.

In some embodiments, control system 76 may compare the pressure to a threshold pressure, wherein the threshold pressure is indicative of a bad filter 200. In some embodiments, control system 76 may compare the flowrate to a threshold flowrate, wherein the threshold flowrate is indicative of a bad filter 200. In another embodiment, control system 76 may compare the ratio of flowrate to pressure to a threshold ratio, wherein the threshold ratio is indicative of a bad filter 200. In yet another embodiment, control system 76 may assess any combination of threshold pressure, threshold flowrate, or threshold ratio of flowrate to pressure. In some embodiments, microprocessor 78 may utilize an algorithm comparing the detected pressure, the detected flowrate, and the ratio of flowrate to pressure to determine whether filter 200 still effectively moves air therethrough.

Control system 76 may provide a visual or audible notification indicating whether filter 200 needs to be replaced at step 111. For example, control system 76 may display an icon on graphical user interface 16. The icon may indicate that filter 200 needs to be replaced or that filter 200 is still usable. In some embodiments, the icon may indicate a general health of filter 200, for example, "Good", "Fair", or "Bad", among other things. In some embodiments, the icon may be color-coded to indicate the health of filter 200, for example: red, if filter 200 should be replaced; green, if filter 200 is still good; or yellow, if filter 200 will need replacement soon. In some embodiments, control system 76 may activate an audible alert if filter 200 is still good or if filter 200 needs to be changed. If filter 200 is still good, therapy is administered at step 113. Device 10 may provide one alert indicating that filter 200 is still operational and a second alert indicating that filter 200 should be replaced. If an alert is provided indicating that filter 200 should be replaced, the user may override such an alert and continue operation of device 10. In such a scenario, a second notification may be provided prompting the user to replace filter 200 in the future, for example, after the current use of filer 200. This second notification may be provided immediately and/or after device 10 is used.

Referring to FIG. 5A, an embodiment of the device 10 includes a magnetic proximity switch 230 which is sometimes referred to as a Hall Effect sensor. Magnetic proximity switch 230 is positioned within housing 12 adjacent to front wall 14, for example, on an inner sidewall of front wall 14. More particularly, magnetic proximity switch 230 is positioned adjacent hose port 24. Magnetic proximity switch 230 may be positioned at any location around hose port 24. Magnetic proximity switch 230 is electrically coupled to control system 76 via leads 77. FIGS. 5A-5B also illustrate an embodiment of filter 200 having a metal end piece 232 coupled thereto. Metal end piece 232 is positioned on an end of filter inlet 204. Referring to FIG. 5B, in some embodiments, metal end piece 232 is clipped or snapped onto the end of filter inlet 204. Particularly, inlet 204 has a recess 23 defined at an end thereof. Metal end piece 232 is clipped and secured to recess 23. Metal end piece 232 is positioned around a perimeter of filter inlet 204 so that filter 200 is positionable at any rotational position on hose port 24. Metal end piece 232 is sized to be positioned around hose port 24 when filter 200 is coupled to device 10 and, more particularly, to hose port 24.

Metal end piece 232 activates magnetic proximity switch 230 when filter inlet 204 is coupled to the hose port 24. Upon coupling filter 200 to device 10, a Hall Effect generated between metal end piece 232 and magnetic proximity switch 230 generates an electrical signal to control system 76. The Hall Effect is generated when filter 200 is secured in an operable position on hose port 24. For example, if filter 200 is not properly secured to hose port 24, a signal is not generated. The electrical signal indicates that filter 200 is properly secured to hose port 24 of device 10. Control system 76 recognizes the signal or lack thereof and provides an indication of whether filter 200 is properly secured to hose port 24. In some embodiments, the indication is provided in the form of an icon on graphical user interface 16. For example, an icon may appear on graphical user interface 16 indicating that filter 200 is properly secured to hose port 24. Conversely, an icon may appear on graphical user interface 16 indicating that filter 200 is not secured to hose port 24. In some embodiments, the indicator may be an audible alarm or notification. In some embodiments, an audible notification may signal upon filter 200 being secured to hose port 24. Conversely, an audible notification may signal when filter 200 is not secured to hose port 24. For example, upon activation of device 10, if filter 200 is not properly secured to hose port 24, the audible notification may sound. In some embodiments, if filter 200 is not properly secured to hose port 24, control system 76 may render device 10 inoperable such that device 10 will not start.

Figure 6:
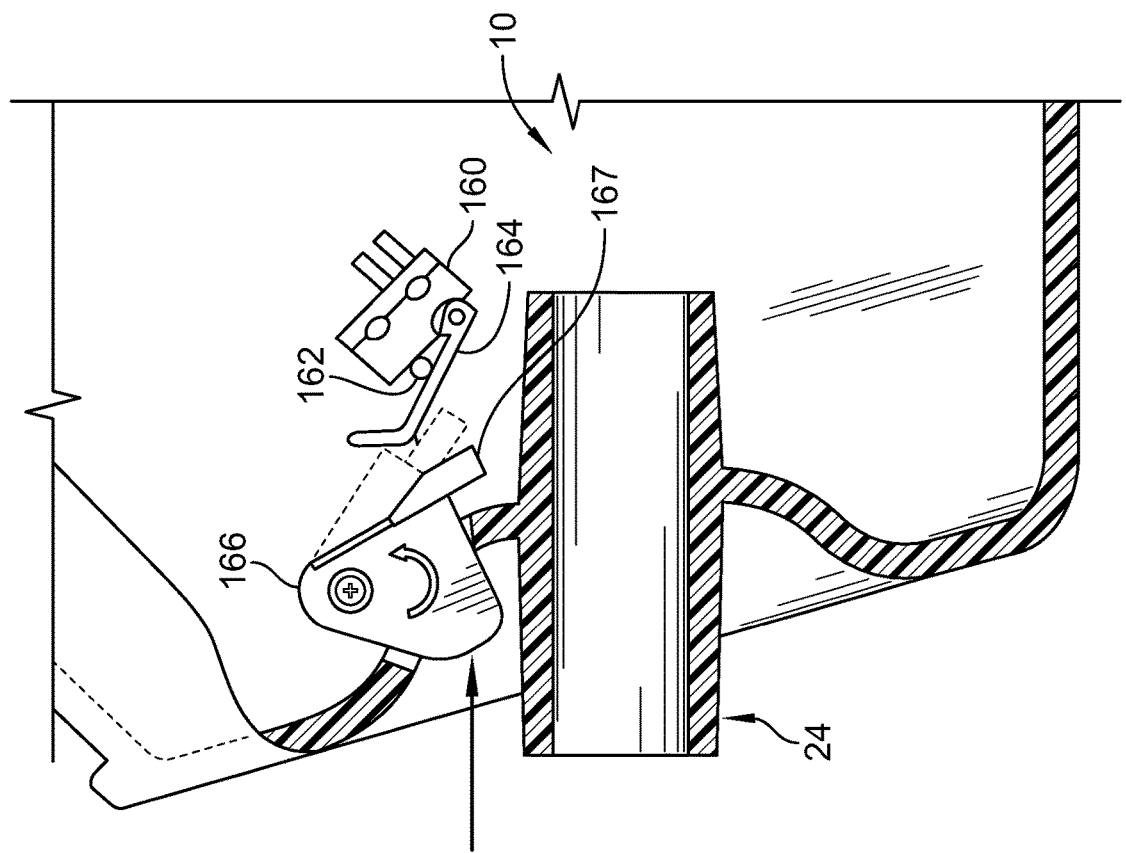
FIG. 6 is a perspective view of yet another embodiment of the device of FIG. 1 having a micro-switch.

Referring to FIG. 6, an embodiment of device 10 includes a micro-switch 160 positioned within the housing 12. Micro-switch 160 is electrically coupled to control system 76. Micro-switch 160 includes an actuator 162 and a lever 164. Lever 164 moves between an open position wherein lever 164 does not engage actuator 162 and a closed position wherein lever 164 engages actuator 162. In some embodiments, lever 164 may engage actuator 162 in the open position, but does not activate actuator 162. In some embodiments, actuator 162 may be a button that is depressed when engaged by lever 164. In some embodiments, actuator 162 may be a magnet and lever 164 may be metal. A Hall-Effect generated by the proximity of the metal lever 164 to the magnetic actuator 162 may activate actuator 162. When actuator 162 is activated a signal is sent to control system 76. A cam 166 having an arm 167 is positioned above hose port 24. Cam 166 rotates from an open position to a closed position. In the open position, cam 166 does not engage lever 164. Alternatively, arm 167 of cam 166 does engage lever 164 in the open position, but does not move lever 164. In the closed position, arm 167 engages lever 164 and moves lever 164 into engagement with actuator 162 so that actuator 162 sends a signal to control system 76.

Upon coupling filter 200 to device 10, filter inlet 204 engages cam 166 to rotate cam 166 into the closed position. In the closed position, cam 166 moves actuator 162 into engagement with actuator 162 so that actuator 162 sends a signal to control system 76. The signal indicates that filter 200 is properly secured to hose port 24. If filter 200 is not properly secured to hose port 24, a signal is not generated. Control system 76 recognizes the signal or lack thereof and provides an indication of whether filter 200 is properly secured to hose port 24. In some embodiments, the indication is provided in the form of an icon on graphical user interface 16. For example, an icon may appear on graphical user interface 16 indicating that filter 200 is properly secured to hose port 24. Conversely, an icon may appear on graphical user interface 16 indicating that filter 200 is not secured to hose port 24. In some embodiments, the indicator may be an audible alarm or notification. In some embodiments, an audible notification may signal upon filter 200 being secured to hose port 24. Conversely, an audible notification may signal when filter 200 is not secured to hose port 24. For example, upon activation of device 10, if filter 200 is not properly secured to hose port 24, the audible notification may sound. In some embodiments, if filter 200 is not properly secured to hose port 24, control system 76 may render device 10 inoperable such that device 10 will not start.

Figure 7:
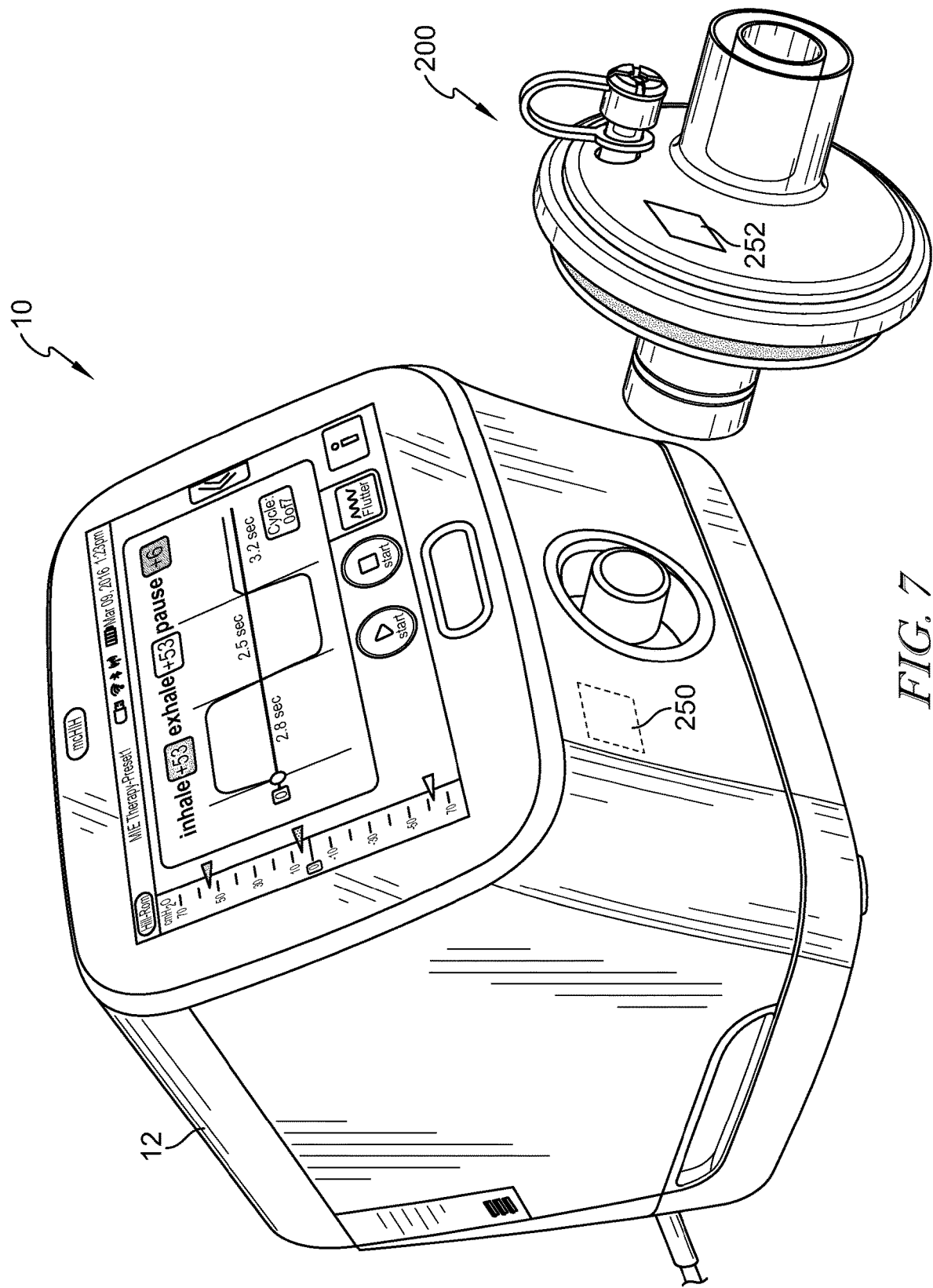
FIG. 7 is a perspective view of yet another embodiment of the device of FIG. 1 having a tag reader, and a further embodiment of the filter of FIG. 3 having an identification tag.

Referring to FIG. 7, an embodiment of device 10 includes a tag reader 250. Tag reader 250 may be positioned within housing 12 or otherwise coupled to housing 12. In some embodiments, tag reader 250 may be part of electrical system 72. Tag reader 250 is electrically coupled to control system 76. In some embodiments, tag reader 250 is not physically coupled to device 10, but communicates with control system 76 of device 10 via a wireless transmission. FIG. 7 also includes an embodiment of filter 200 that includes an identification tag 252. Identification tag 252 may be positioned within filter 200 or otherwise coupled thereto. In some embodiments, identification tag 252 is a radio-frequency identification (RFID) tag and tag reader 250 is a radio-frequency identification (RID) tag reader. Identification tag 252 and tag reader 250 may communicate wirelessly through near-field communication, among other forms of wireless communication.

An RFID integrated circuit chip, either by itself or coupled to an antenna or mounted to a substrate such as a substrate having an antenna, are all considered to be examples of an RFID tag 252 according to this disclosure. Thus, an RFID integrated circuit chip and antenna may be molded into or separately attached to filter 200 without the use of any substrate and still be considered an RFID tag 252. Alternatively, a generally rigid substrate or a generally flexible substrate, such as a sticker, may carry the RFID integrated circuit chip and antenna and be considered an RFID tag 252 according to this disclosure. In some embodiments, the RFID tag 252 is passive so as to be powered by energy emitted from reader 250 and in other embodiments RFID tag 252 is active so as to be powered by its own power source such as a battery or photovoltaic cell.

When filter 200 is coupled to device 10, identification tag 252 communicates with tag reader 250 so that control system 76 identifies filter 200. Each filter 200 that may be used with device 10 contains its own unique identification number associated therewith. Accordingly, when tag reader 250 reads identification tag 252, control system 76 of device 10 identifies the particular filter 200. By providing each filter 200 with its own unique identification number, filters 200 can be tracked. For example, a medical facility may have multiple filters 200 that are each designated for a unique patient. By identifying filter 200 through the identification number, the medical facility can ensure that the appropriate filter 200 is used with the correct patient.

Control system 76 can track the usage of each filter 200. Once filter 200 is identified by the tag reader 250, control system 76 can track a number of times that filter 200 is used. The control system 76 can also track an overall time that the filter 200 has been used, for example a half hour, an hour, etc. In some embodiments, memory 80 stores the number of times that each filter 200 has been used and/or the overall amount of time that the filter has been used. For example, if a new filter 200 is coupled to device 10, control system 76 identifies the filter 200 as new and not as having been used. Device 10 is then operated with filter 200 attached thereto. Each time that device 10 is operated with filter 200 attached thereto, control system 76 stores usage data in memory 80. If a filter 200 is coupled to device 10 and used for three therapeutic sessions, control system 76 will store in memory 80 a log that filter 200 has been used three times. The next subsequent time that filter 200 is coupled to device 10, control system 76 will identify filter 200 as having been used three times. The control system 76 may also display the number "3" on graphical user interface 16 to notify a user of the number of times that filter 200 has been used. If filter 200 is used an additional three times during this subsequent usage, control system 76 will update the log in memory 80 to indicate that filter 200 has been used six total times. Alternatively or additionally, control system logs an accumulated amount of time that filter 200 has been used and displays the accumulated time on graphical user interface 16.

Figure 8:
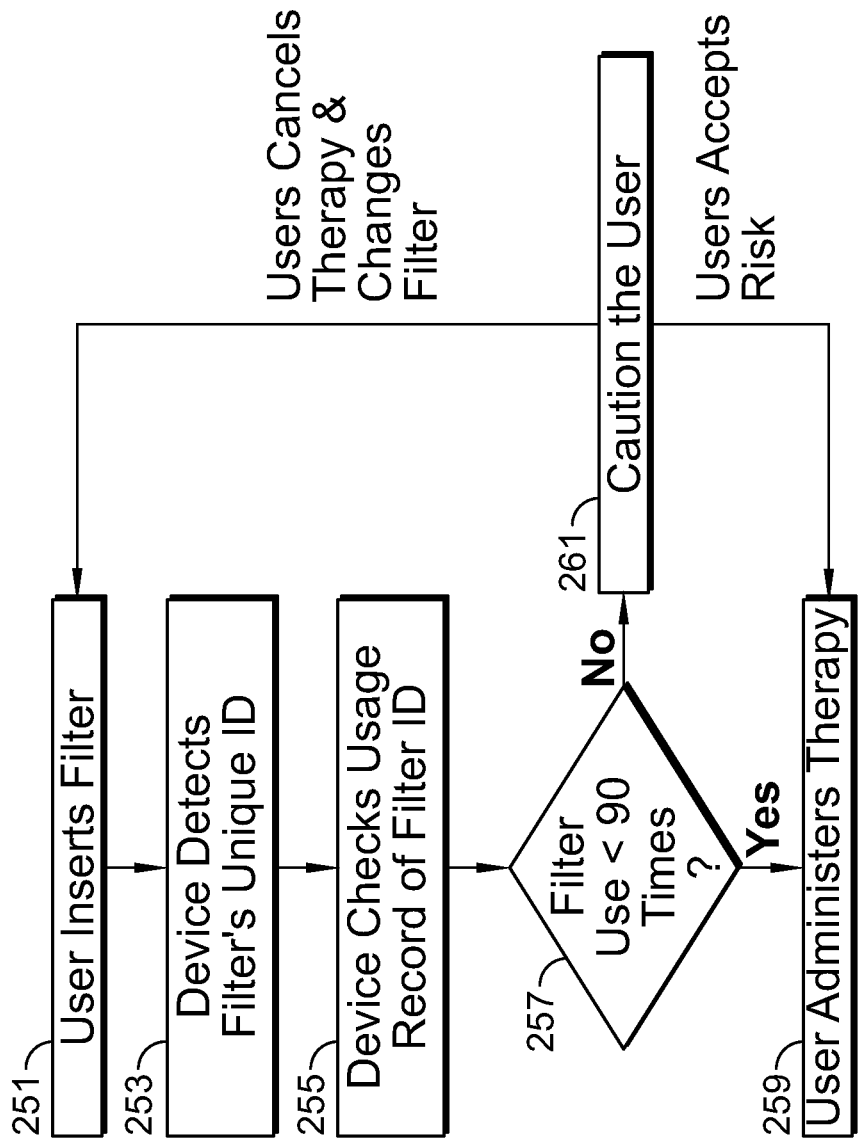
FIG. 8 is a flowchart for assessing the health of the filter of FIG. 7.

Referring to FIG. 8, by tracking a usage of filter 200, the general health or condition of filter 200 can be monitored so that filter 200 can be changed as necessary. At step 251, a filter 200 may be coupled to device 10 and detected by device 10 at step 253. Control system 76 identifies filter 200 at step 253 and then determines the usage record of filter 200 based on the usage record stored in memory 80 at step 255. Control system 76 then determines, at step 257, whether filter 200 has been used more than a predetermined threshold number of times (and/or more than a threshold accumulated amount of time). If the filter usage has not exceeded the threshold, therapy is administered as scheduled at step 259. In some embodiments, if filter 200 has been used more than a threshold number of times, a visual or audible notification is provided at step 261.

In some embodiments, a visual or audible notification may be provided if the filter usage is approaching the threshold. In some embodiments, the threshold number may be ninety uses. When filter 200 is identified as having been used ninety times, display 16 will provide the notification. In some embodiments, a notification is provided if the filter usage is reaching ninety, for example, after the eightieth use. By monitoring filter usage through tracking a number of times that filter 200 has been used, a healthcare professional may determine whether filter 200 needs to be changed prior to filter 200 becoming ineffective. In some embodiments, a similar determination can be made based on accumulated amount of time that filter 200 has been used.

Figure 9:
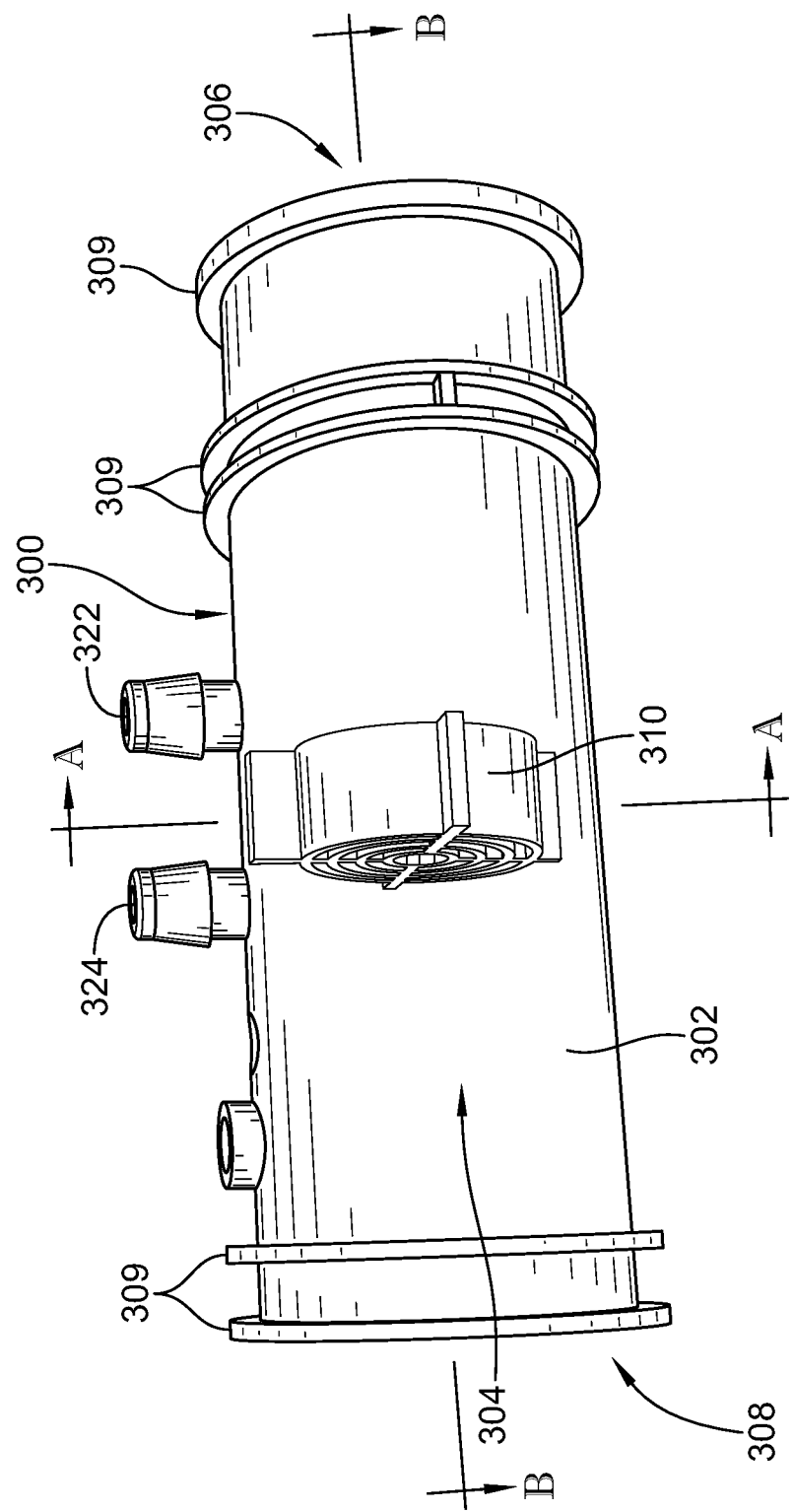
FIG. 9 is a perspective view of an embodiment of a laminar flow structure that may be used with the respiratory device of FIG. 1.
Figure 10:
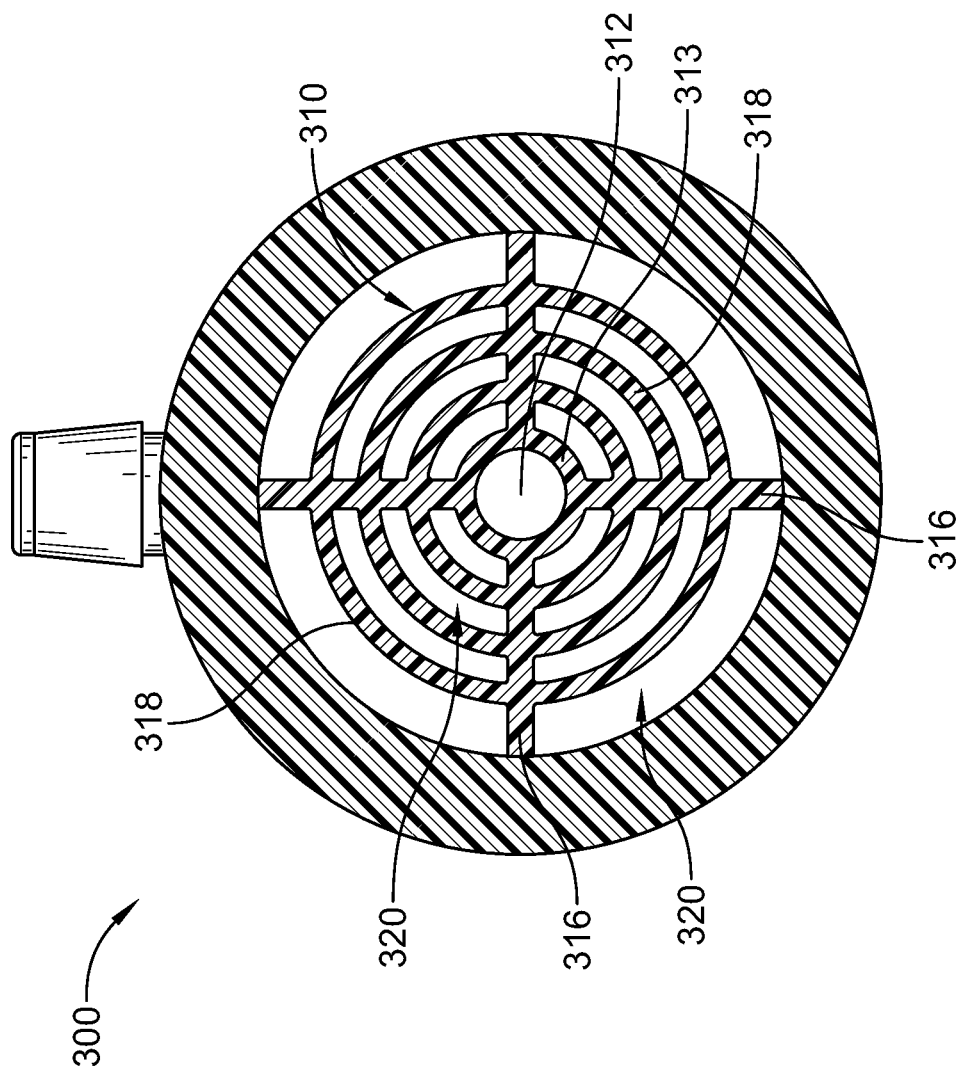
FIG. 10 is a front cross-sectional view of the laminar flow structure taken along a line A-A of FIG. 9.
Figure 11:
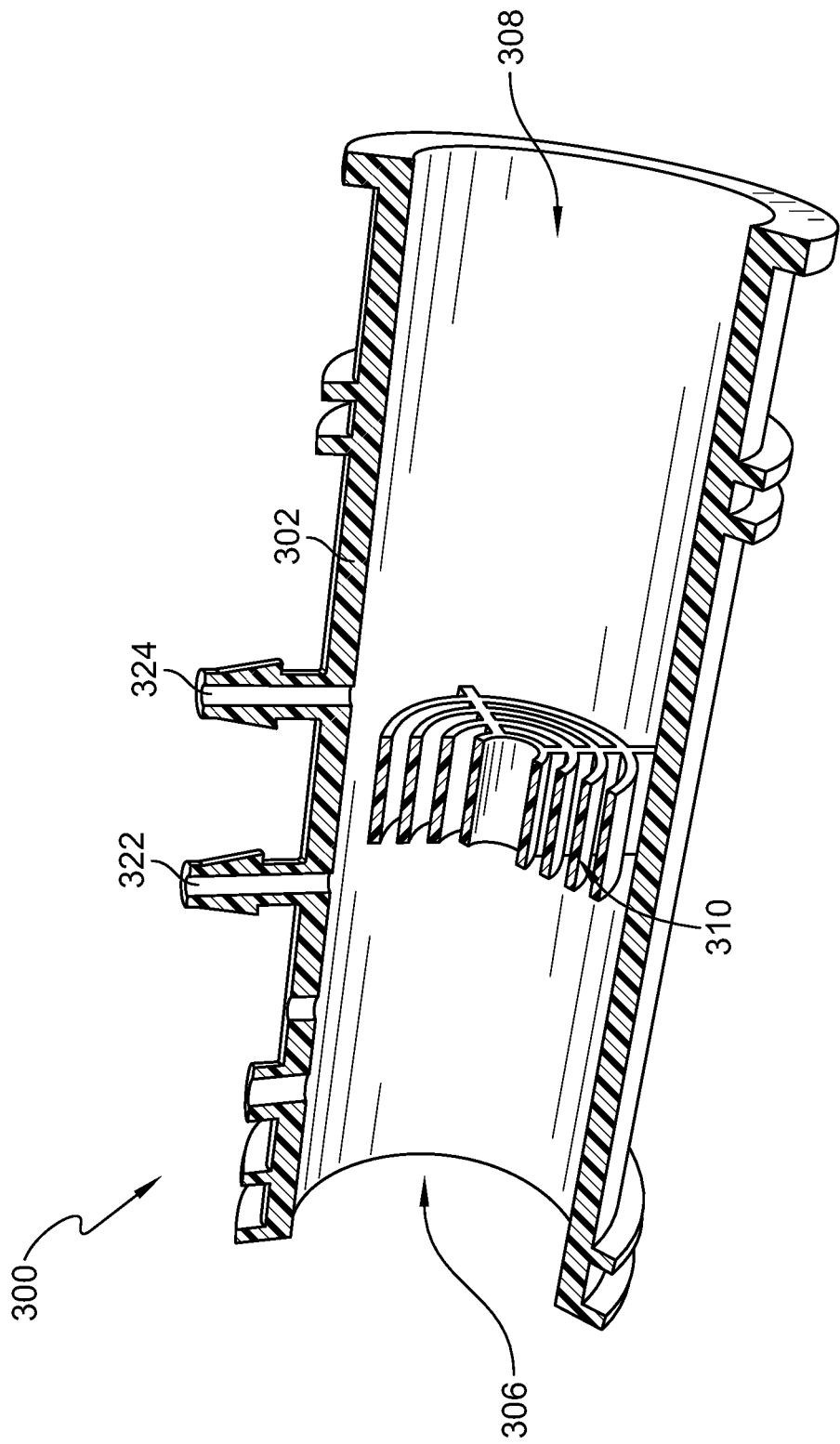
FIG. 11 is a perspective cross-sectional view of the laminar flow structure taken along a line B-B of FIG. 9.

Referring now to FIGS. 9-11, a laminar flow structure 300 for device 10 is configured to be positioned in flow communication with hose port 24. Laminar flow structure 300 includes a cylindrical body 302 defining a chamber 304 that extends between an inlet 306 and an outlet 308. Attachment flanges 309 extend radially outwardly from cylindrical body 302. Attachment flanges 309 extend entirely around a circumference of cylindrical body 302 in the illustrative embodiment. In some embodiments, attachment flanges 309 may extend only partially around cylindrical body 302. Cylindrical body 302 has an axis 303 extending therethrough. Inlet 306 is positioned at an end of hose port 24 that couples to blower 86, and outlet 308 is positioned at an end of hose port 24 that couples to hose 20. Laminar flow structure 300 is configured to convert airflow discharged from blower 86 into a laminar airflow.

Laminar flow structure 300 includes a vent 310 positioned therein. Particularly, vent 310 is positioned within chamber 304 between inlet 306 and outlet 308. Vent 310 is structurally designed to convert the airflow from blower 86 into laminar airflow. Vent 310 includes a central aperture 312 defined by a central ring 313 as shown in FIG. 10. A plurality of spokes 316 extends radially outwardly from central ring 313. In some embodiments, at least one spoke 316 extends radially outwardly from central aperture 312. In some embodiments, any number of spokes 316 extends radially outwardly from central aperture 312. In the illustrative embodiment, vent 310 includes four spokes 316 formed in a plus-sign configuration. A plurality of vanes 318 extends circumferentially about central ring 313 so as to be concentric with ring 313. In some embodiments, at least one vane 318 extends circumferentially about central ring 313. The vanes 318 form a plurality of outer rings surrounding the central ring 313. The vanes 318 extend between the spokes 316 and form arcuate slots 320 therebetween. In some embodiments, the structure of vent 310 may be described as a bulls-eye configuration. Air flowing through the central aperture 312 and the slots 320 takes a laminar airflow profile.

A first sensor outlet 322 and a second sensor outlet 324 extend radially outwardly from cylindrical body 302 of laminar flow structure 300 as shown in FIGS. 9 and 11. First sensor outlet 322 is positioned upstream of vent 310, and second sensor outlet 324 is positioned downstream of the vent 310. First sensor outlet 322 is positioned between vent 310 and inlet 306 of laminar flow structure 300, and second sensor outlet 324 is positioned between vent 310 and outlet 308 of laminar flow structure 300. In some embodiments, first sensor outlet 322 and second sensor outlet 324 are aligned along a line extending parallel to axis 303 of laminar flow structure 300. In some embodiments, first sensor outlet 322 and second sensor outlet 324 are misaligned with respect to a line extending parallel to axis 303 of laminar flow structure 300. In some embodiments, laminar flow structure 300 includes a plurality of first sensor outlets 322 and/or a plurality of second sensor outlets 324.

Figure 12:
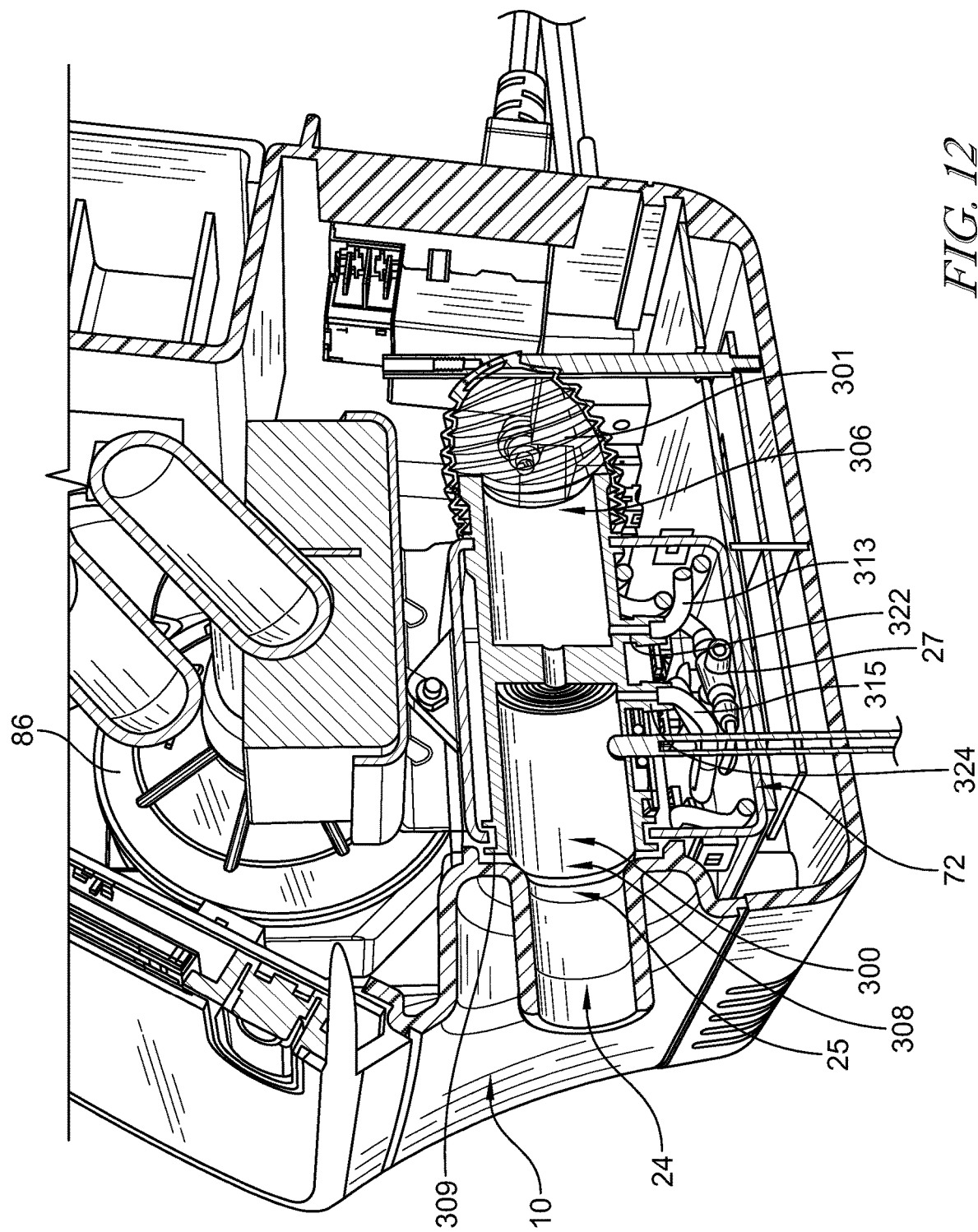
FIG. 12 is a cross-sectional view of the respiratory device of FIG. 1 having the laminar flow structure of FIG. 9 positioned therein.

Referring now to FIG. 12, laminar flow structure 300 is positioned within device 10 adjacent to hose port 24. Laminar flow structure 300 is positioned at an inlet 25 of hose port 24 so that laminar flow structure 300 is in flow communication with hose port 24. Outlet 308 of laminar flow structure 300 is coupled to inlet 25 of hose port 24. A conduit 301 extends from inlet 306 of laminar flow structure 300 to blower 86 so that air discharged from blower 86 passes through laminar flow structure 300 prior to passing through hose port 24. Blower 86, conduit 301, laminar flow structure 300, and hose port 24 are all coupled in a substantially airtight configuration. When placed within device 10, attachment flanges 309 are coupled to a housing 27 of electrical system 72. Attachment flanges 309 extend around the circumference of cylindrical body 302 such that laminar flow structure 300 may be positioned in any rotational position within device 10. In the illustrative embodiment, laminar flow structure 300 is positioned such that sensor outlets 322 and 324 face downwardly within the device 10. In some embodiments, sensor outlets 322 and 324 may face any direction within device 10. Sensor outlets 322 and 324 are coupled to conduits 311 and 315 respectively, which join laminar flow structure to components of electrical system 72 and/or control system 76 that may be utilized to measure pressure or flowrate.

Figure 13:
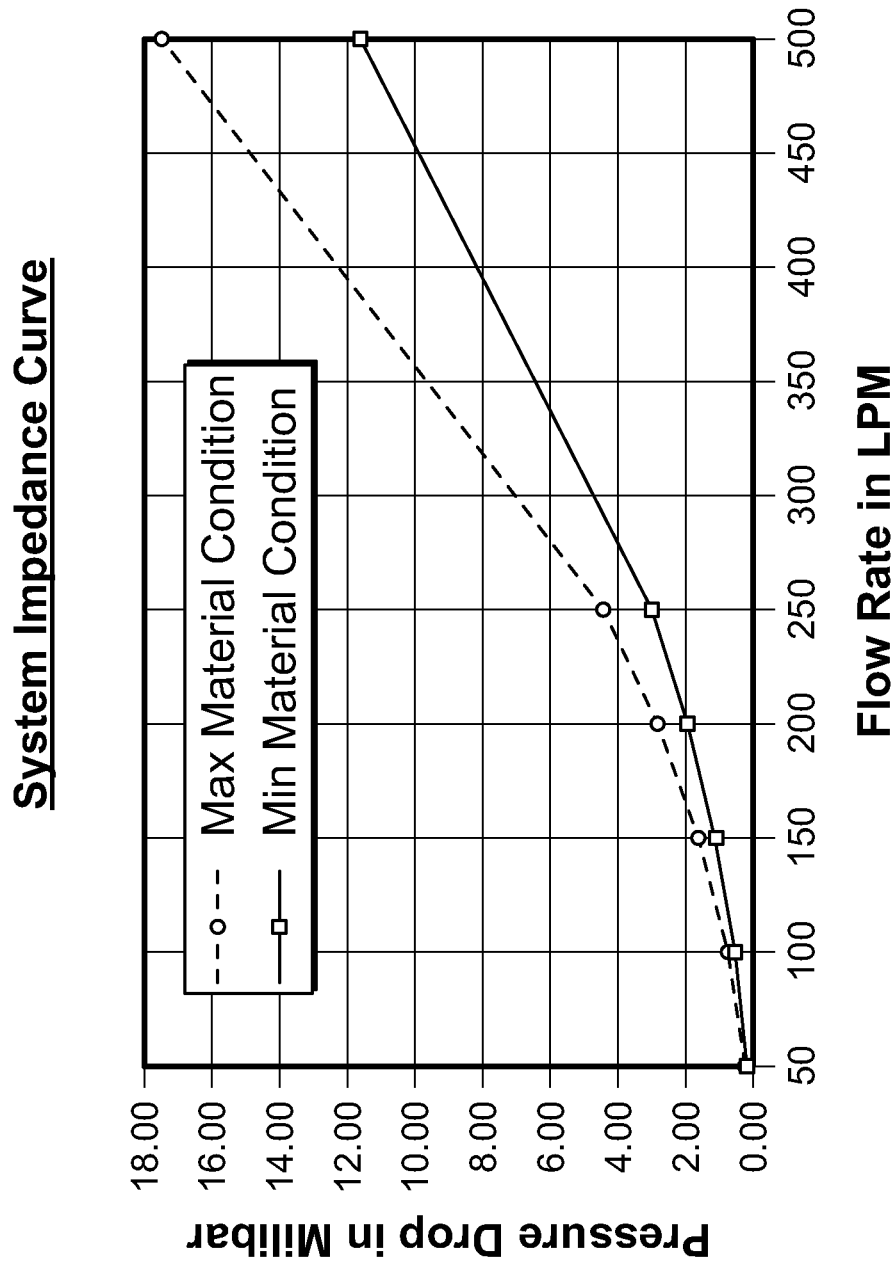
FIG. 13 is a graph illustrating a flowrate versus a pressure drop through the laminar flow structure of FIG. 9.

Referring to FIG. 13, first sensor outlet 322 and second sensor outlet 324 are each in flow communication with sensors 150, so that sensors 150 can determine a pressure and a flowrate of airflow at both first sensor outlet 322 and second sensor outlet 324. In particular, the pressure and flowrate of airflow is measured both upstream of vent 310 at first sensor outlet 322, and downstream of vent 310 at second sensor outlet 324. Control system 76 may compare the pressure and flowrate of airflow at first sensor outlet 322 to the pressure and flowrate of airflow at second sensor outlet 324 to determine whether a pressure drop or flowrate drop is caused by vent 310. By measuring pressure drop and flowrate drop, control system 76 can determine whether laminar airflow is being achieved and maintained within laminar flow structure 300. FIG. 13 illustrates impedance curves for laminar flow structure 300 under minimum and maximum flowrate to pressure conditions. In some embodiments, laminar flow structure 300 maintains a laminar airflow having a maximum pressure of approximately 80 cmH$_2$O when the flowrate is between approximately 160 and approximately 180 liters per minute. In some embodiments, laminar flow structure 300 maintains a laminar airflow having a maximum pressure of approximately 80 cmH$_2$O when the flowrate is between approximately 170 and approximately 190 liters per minute. In some embodiments, laminar flow structure 300 maintains a laminar airflow having a maximum pressure of approximately 80 cmH$_2$O when the flowrate is between approximately 160 and approximately 190 liters per minute.

Figure 14:
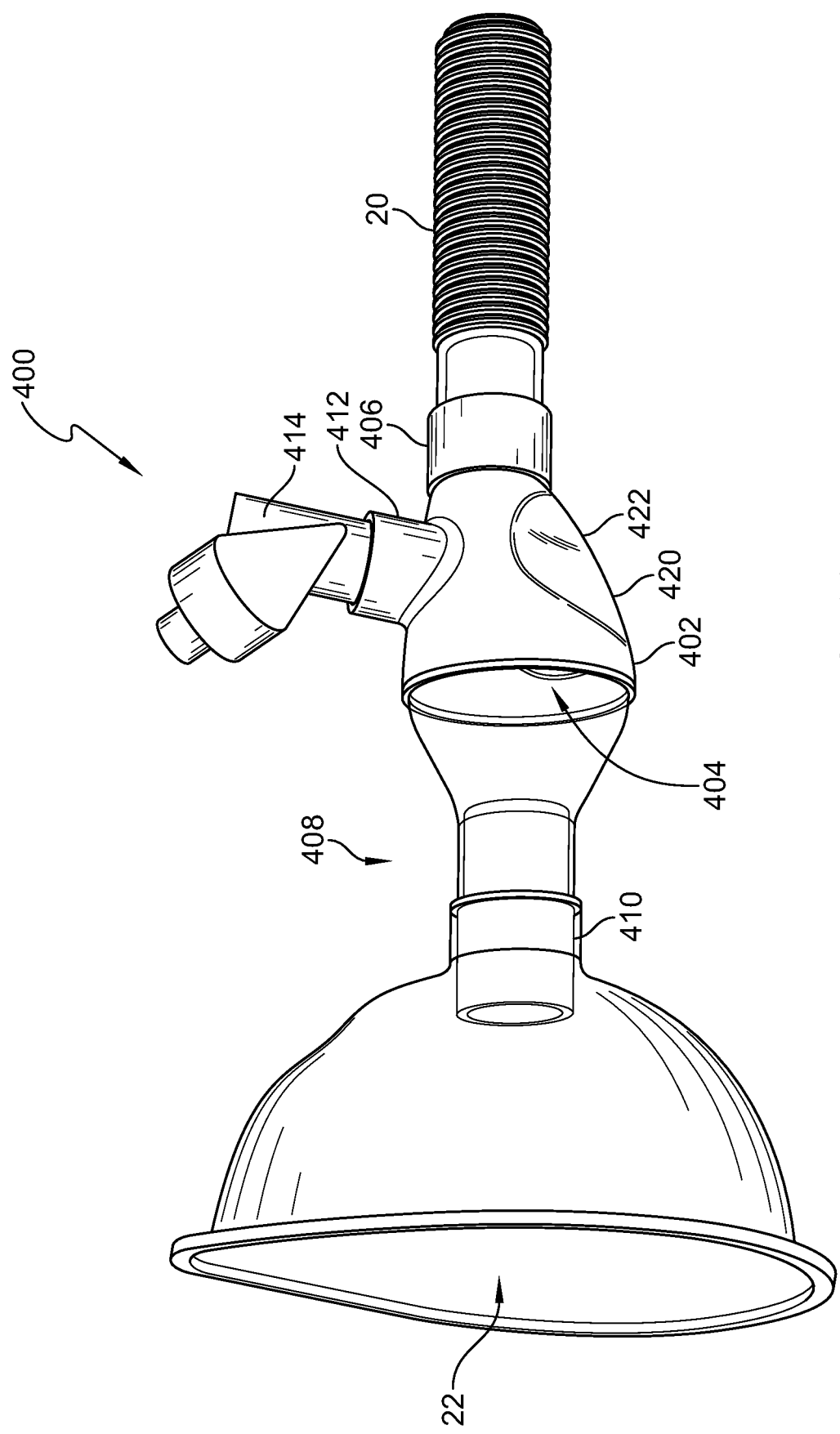
FIG. 14 is a perspective view of an embodiment of a nebulizer assembly that may be used with the respiratory device of FIG. 1.
Figure 15:
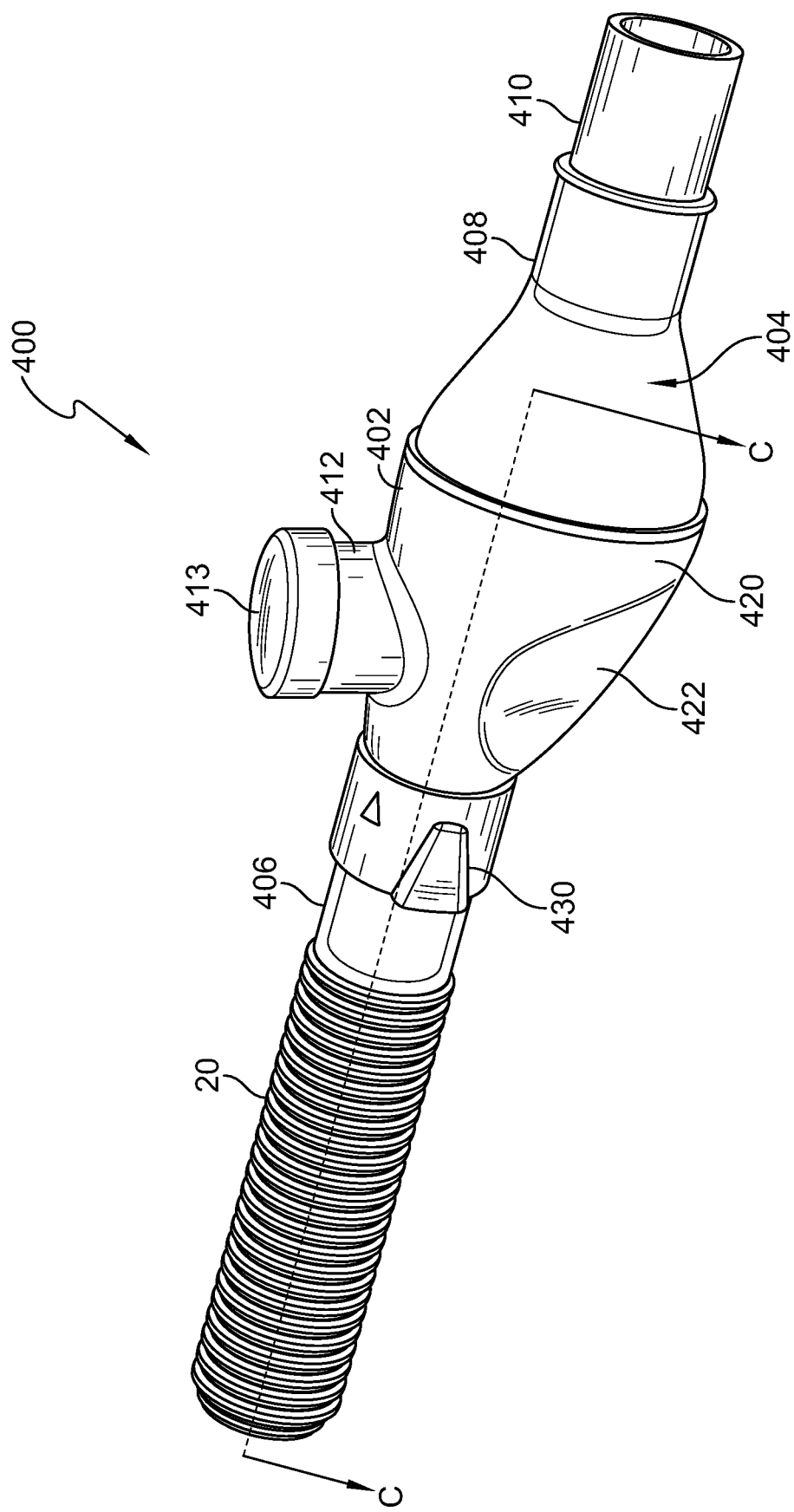
FIG. 15 is a perspective view of the nebulizer assembly of FIG. 13 having a nebulizer cap and occlusion ring.
Figure 16:
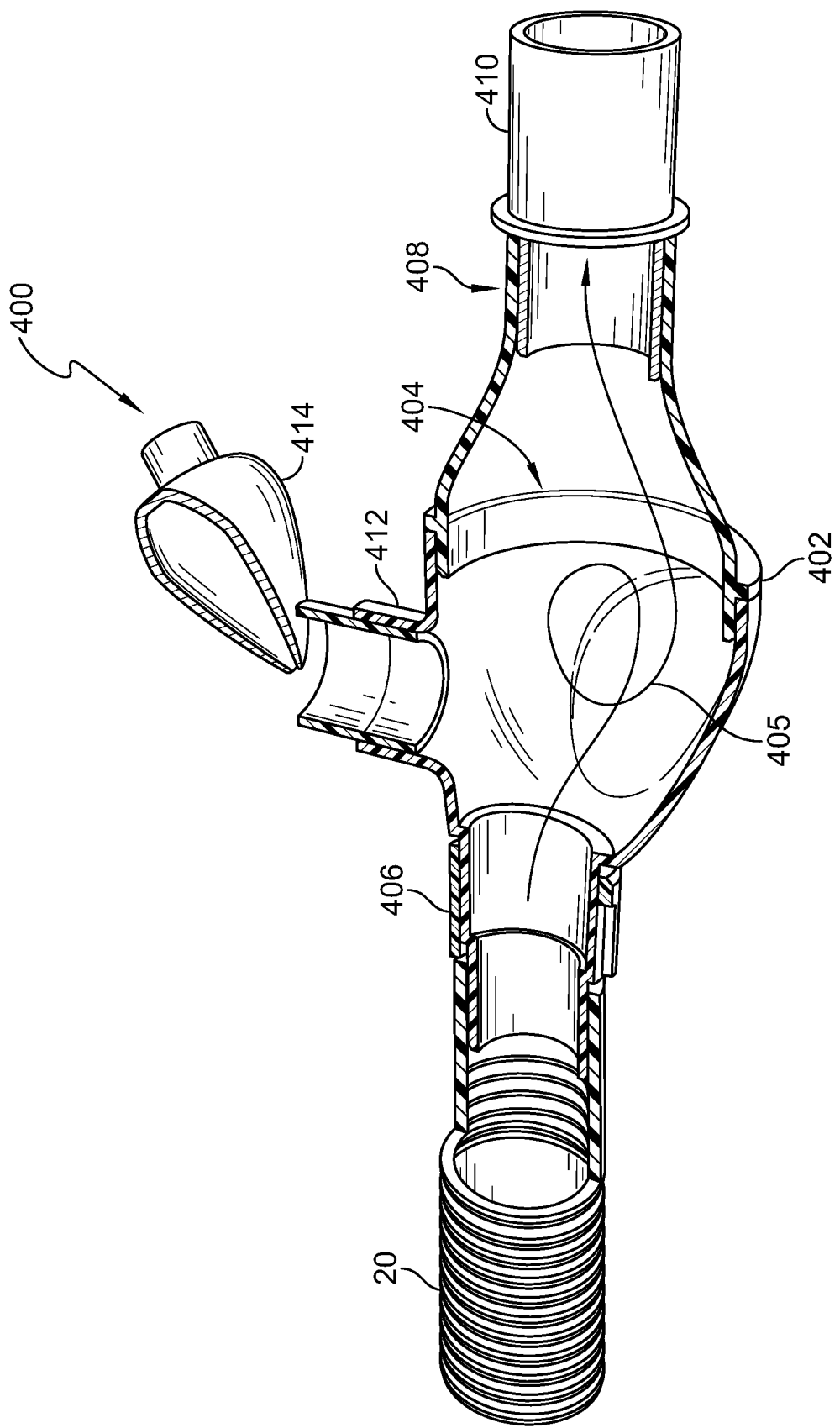
FIG. 16 is a cross-sectional view of portions of the nebulizer assembly taken along line C-C of FIG. 14.
Figure 17:
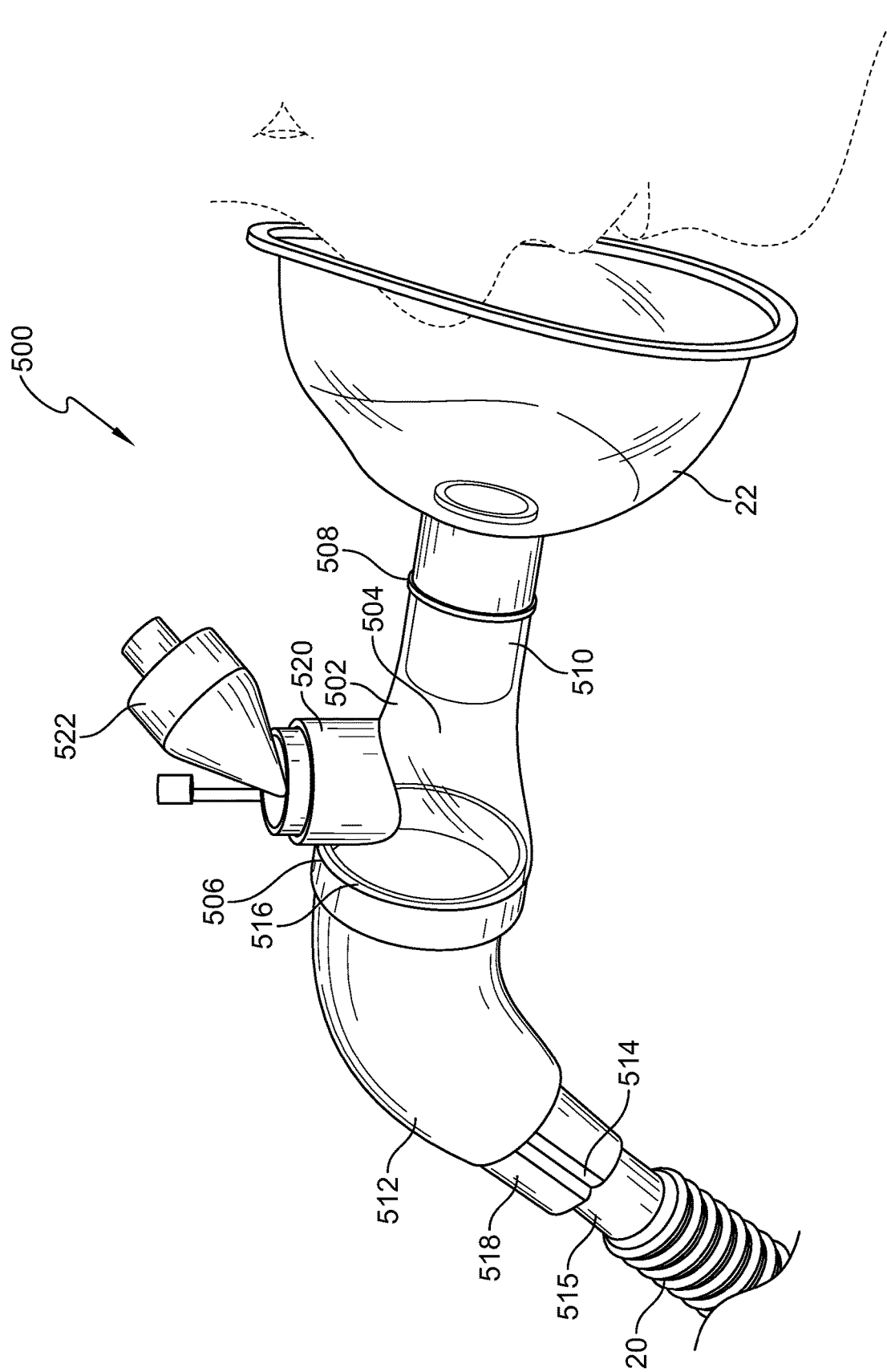
FIG. 17 is a perspective view of another embodiment of a nebulizer assembly that may be used with the respiratory device of FIG. 1.

Referring to FIGS. 14-16, device 10 includes a nebulizer assembly 400. Assembly 400 includes a housing 402 defining a chamber 404. An inlet 406 and an outlet 408 are in flow communication with the chamber 404. The inlet 406 is positioned on a back side of the housing 402, and the outlet 408 is positioned on an opposite front side of the housing 402. The inlet 406 and the outlet 408 are linearly offset. That is, a central axis defined by inlet 406 is offset from, and substantially parallel with a central axis defined by outlet 408. The inlet 406 couples to hose 20 extending from device 10. In some embodiments, hose 20 is substantially non-linear to produce turbulent airflow therethrough. Patient interface 22 is coupled to outlet 408 of assembly 400. An adapter 410 may be coupled to outlet 408. Adapter 410 is configured to couple to patient interface 22, for example, a mask or mouthpiece used by a patient. Air flows from hose 20 to adapter 410 via assembly 400. The linearly offset inlet 406 and outlet 408 of housing 402 facilitates turbulent airflow 405 being produced within chamber 404 to mix the air flowing therethrough, as illustrated in FIG. 16.

The housing 402 also includes a nebulizer port 412 in flow communication with chamber 404. Nebulizer port 412 is positioned between inlet 406 and outlet 408. Nebulizer port 412 is positioned on a top of housing 402 in the illustrative example. In some embodiments, nebulizer port 412 is positioned on a side or bottom of housing 402. Nebulizer port 412 is configured to receive a nebulizer 414 therein to produce atomized medication. For example, the nebulizer 414 may be a jet nebulizer, an ultrasonic wave nebulizer, or a vibrating mesh nebulizer. The turbulent airflow produced within chamber 404 facilitates mixing the airflow with the atomized medication. Nebulizer port 412 may include a removable cap 413 (shown in FIG. 15) so that assembly 400 may be used without a nebulizer 414 but with the nebulizer port being closed off from the ambient atmosphere.

Housing 402 includes an outer surface 420 having a grip 422 defined therein by a recess. Grip 422 is configured for a user to position their thumb thereon. In some embodiments, grip 422 is provided on opposite sides of housing 402 so that one of the grips 422 may be configured for the user to place one or more fingers thereon. In some embodiments, housing 402 may include any number of grips 422 for their thumb or any number of fingers. Finger grip 422 is formed in a side of housing 402 so that a user may grip housing 402 with their right hand with adapter 410 facing toward the user. In some embodiments, grip 422 may be formed on an opposite side of housing 402 so that a user may grip housing 402 with their left hand with adapter 410 facing toward the user.

In some embodiments, an occlusion ring 430 may be coupled to inlet 406 as illustrated in FIG. 15. Hose 20 is coupled to port 406 adjacent to occlusion ring 430. Occlusion ring 430 is rotatable to open and close a side vent hole (not shown) formed in inlet 406. By closing the vent hole with occlusion ring 430, assembly 400 is operational for air to flow therethrough. By opening the vent hole with occlusion ring 430, air is discharged through the vent hole prior to entering chamber 404. Discharging the air enables a user to lessen the pressurized air delivery of assembly 400 by rotating occlusion ring 430 if the user is struggling to breathe with assembly 400. Once the user is comfortable, occlusion ring 430 may be rotated back to close the vent hole and resume treatment. When the vent hole is opened with the occlusion ring 430, some or all of the user's exhaled breath may escape to atmosphere through the vent hole.

Referring to FIG. 17, device 10 includes another embodiment of a nebulizer assembly 500. Assembly 500 includes a housing 502 defining a chamber 504. An inlet 506 and an outlet 508 are formed at opposite ends of housing 502 and are in flow communication with chamber 504. Inlet 506 has a larger circumference than outlet 508. In some embodiments, inlet 506 and outlet 508 may have any suitable circumference. In some embodiments, the circumference of inlet 506 and the circumference of outlet 508 give housing 502 a substantially frusto-conical shape. Hose 20 couples to inlet 506. An adapter 510 may be coupled to outlet 408. Adapter 510 is configured to couple to patient interface 22, for example a mask or mouthpiece used by a patient. In some embodiments, hose 20 is substantially non-linear to produce turbulent airflow therethrough.

Air flows from hose 20 to adapter 510 via assembly 400. A handle 512 is provided between the inlet 506 and hose 20 interface. Handle 512 is curved between a handle inlet 514 and a handle outlet 516. Handle outlet 516 has a larger circumference than handle inlet 514. In some embodiments, handle inlet 514 and handle outlet 516 have any suitable circumference. In some embodiments, handle 512 may be defined as being substantially banana-shaped. Handle inlet 514 is coupled to hose 20, and handle outlet 516 is coupled to inlet 506 of housing 502. Handle inlet 514 includes a selector ring 515 that rotates to release air flow therefrom. When housing 502 is gripped by a user, outlet 508 of housing 502 faces substantially horizontally, handle 512 positions handle inlet 514 in a downward facing position. In this position, hose 20 is coupled to handle 512 such that hose 20 extends substantially vertically thereby allowing a patient to comfortably hold assembly 500 without strain or pulling on hose 20.

Figure 18:
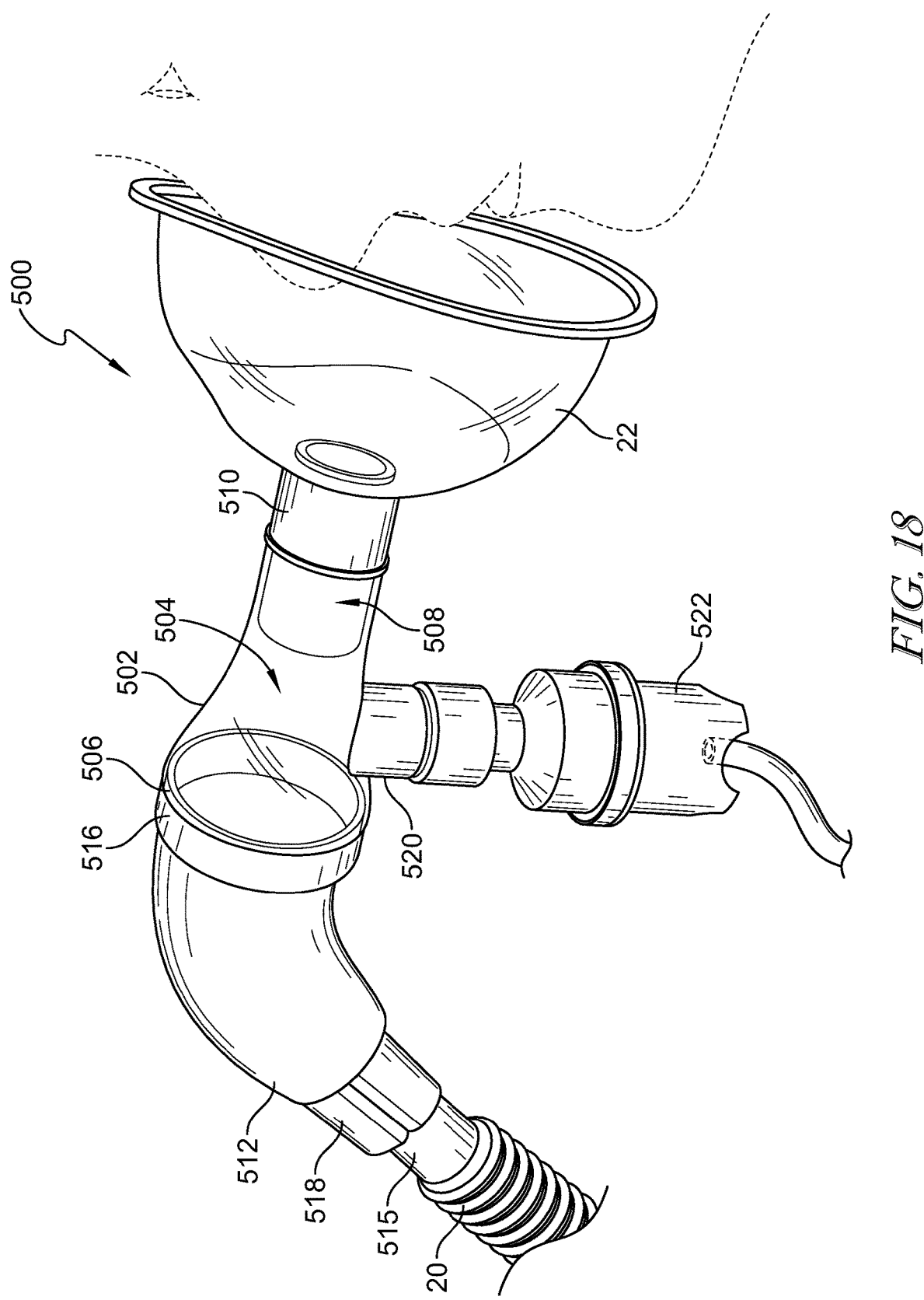
FIG. 18 is a perspective view of the nebulizer assembly of FIG. 17 having the housing rotated for use with pneumatically operated nebulizer.
Figure 19:
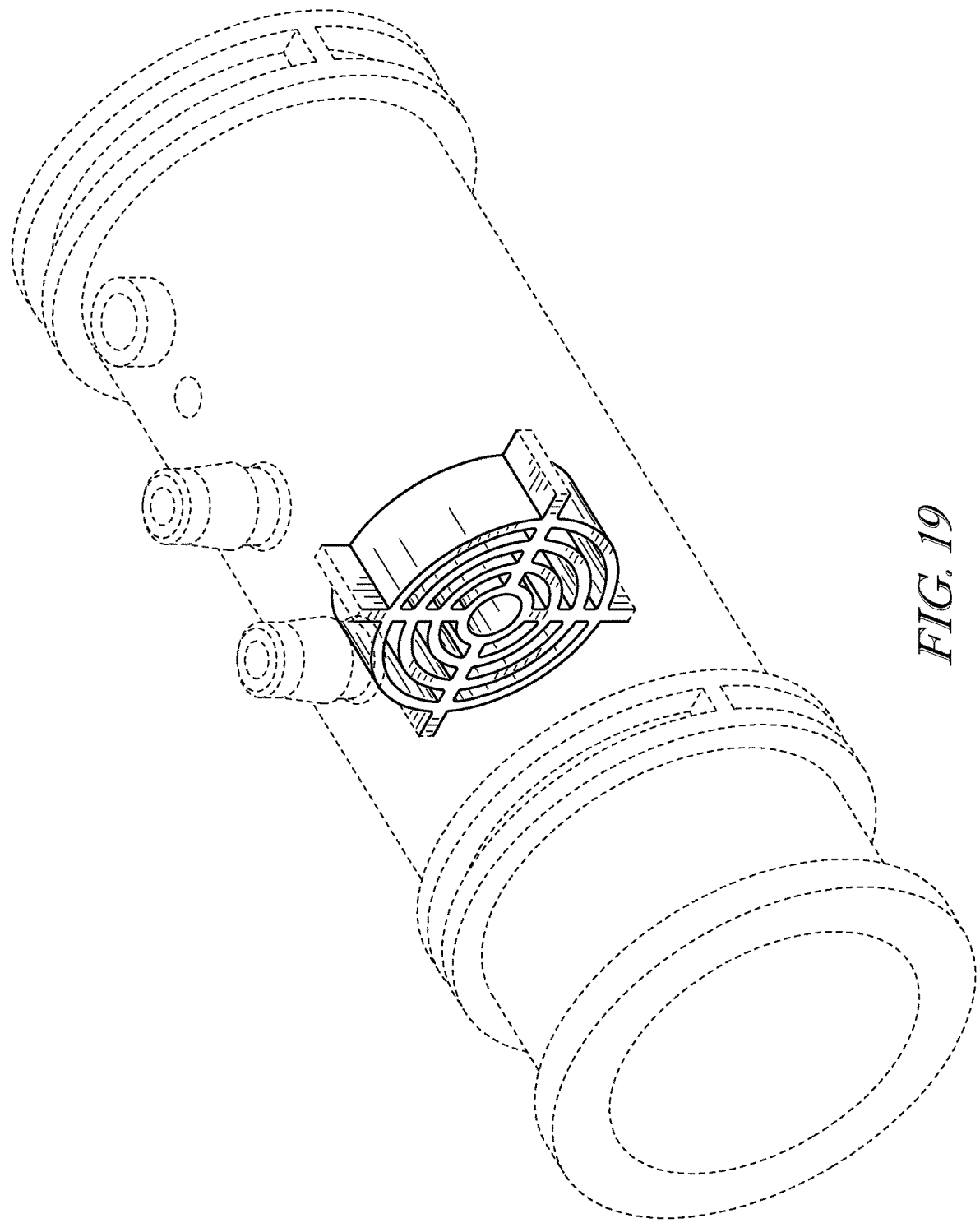
Figure 20:
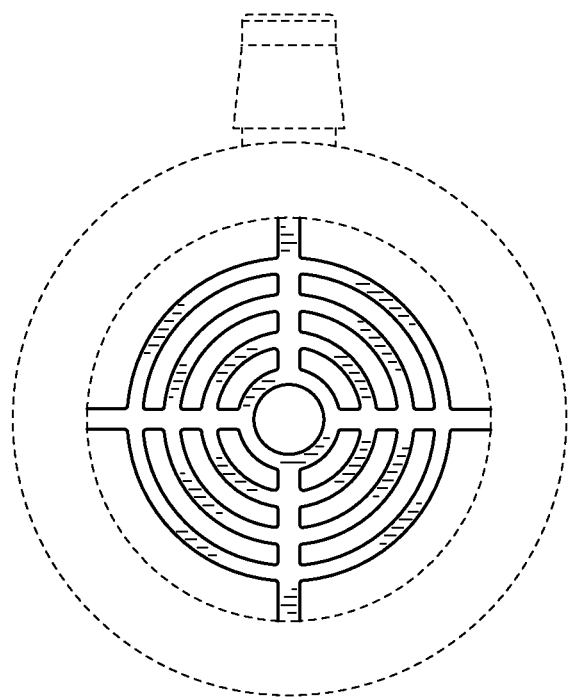
Figure 21:
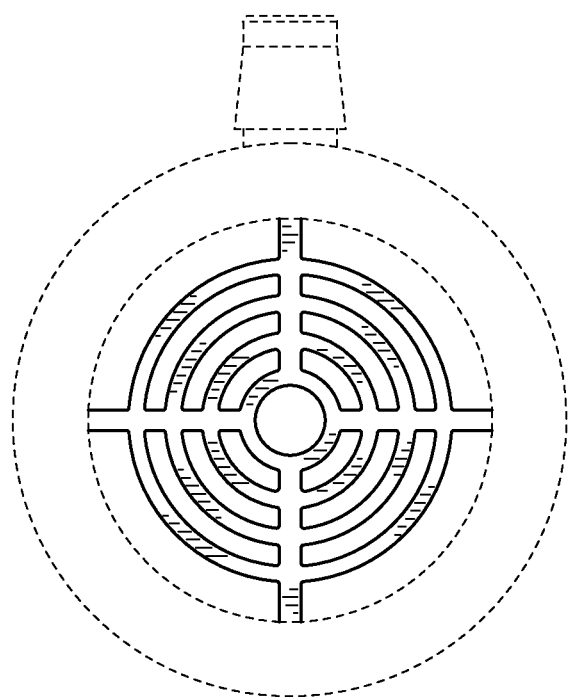
Figure 22:
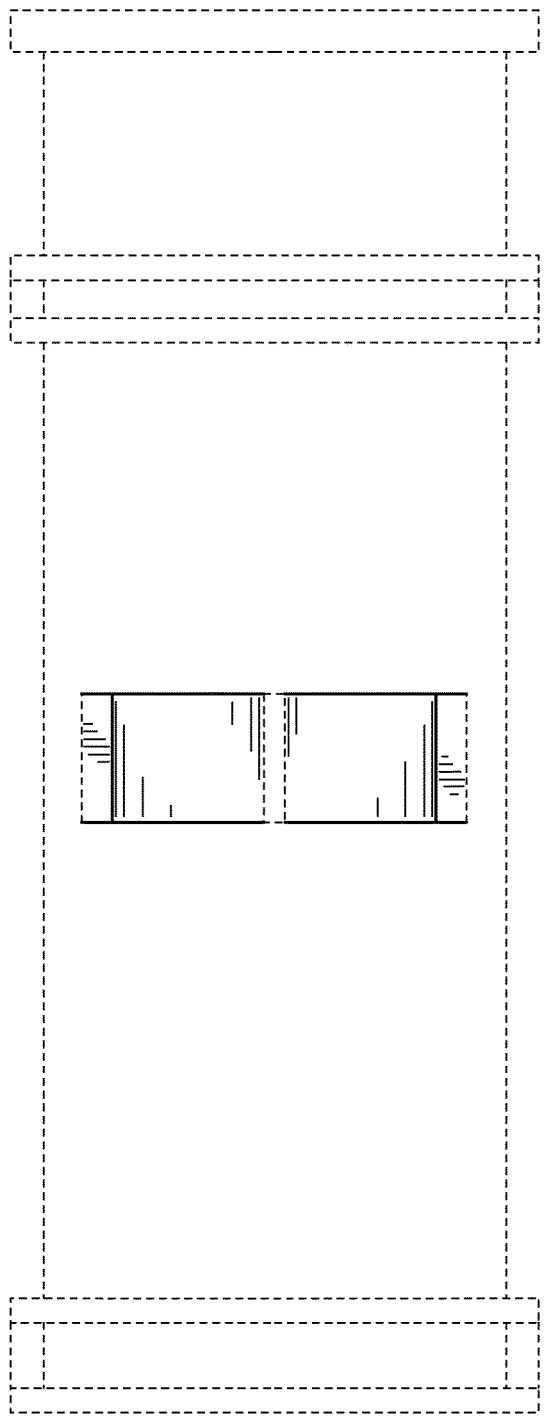
Figure 23:
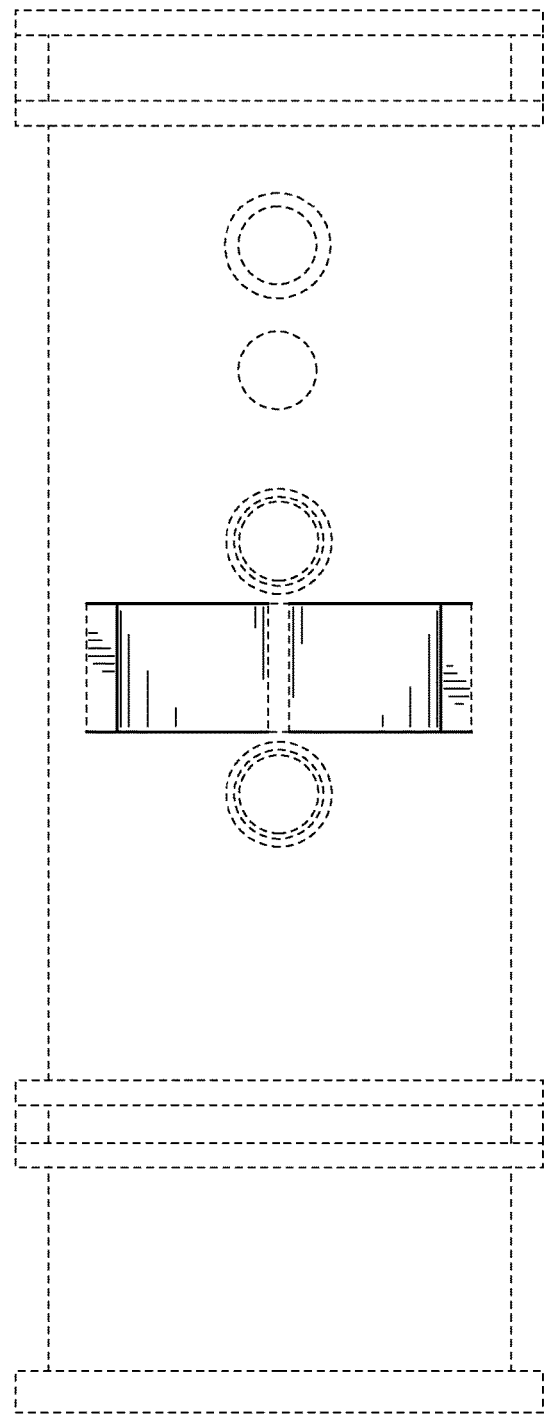
Figure 24:
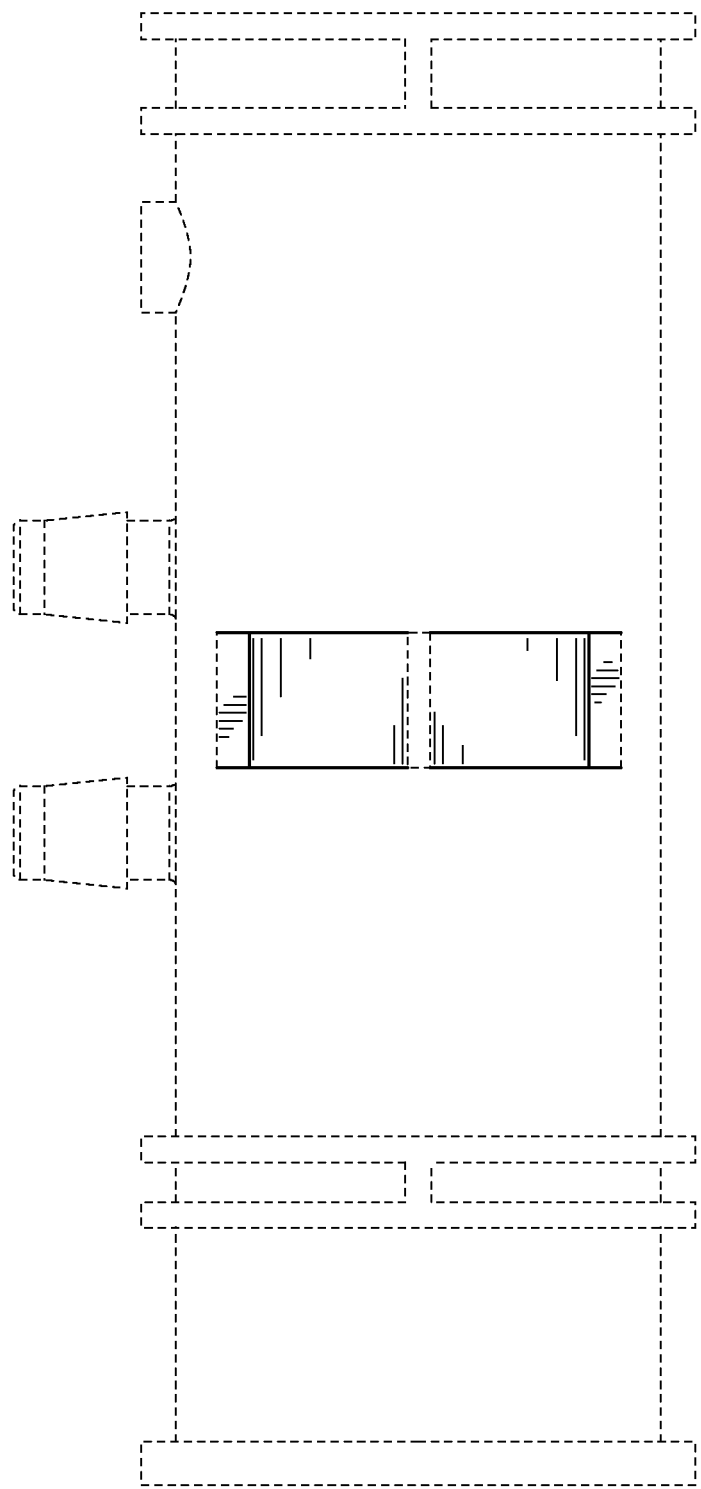
Figure 25:
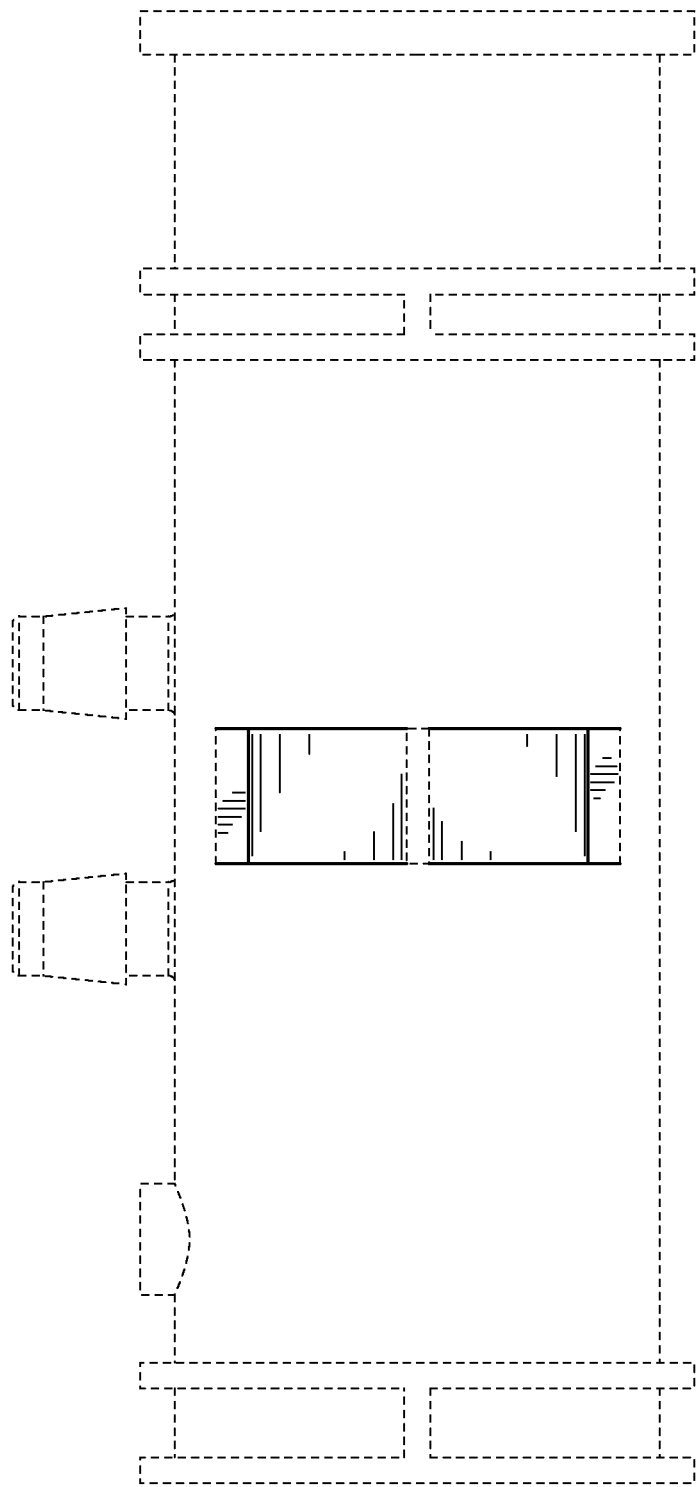
Figure 26:
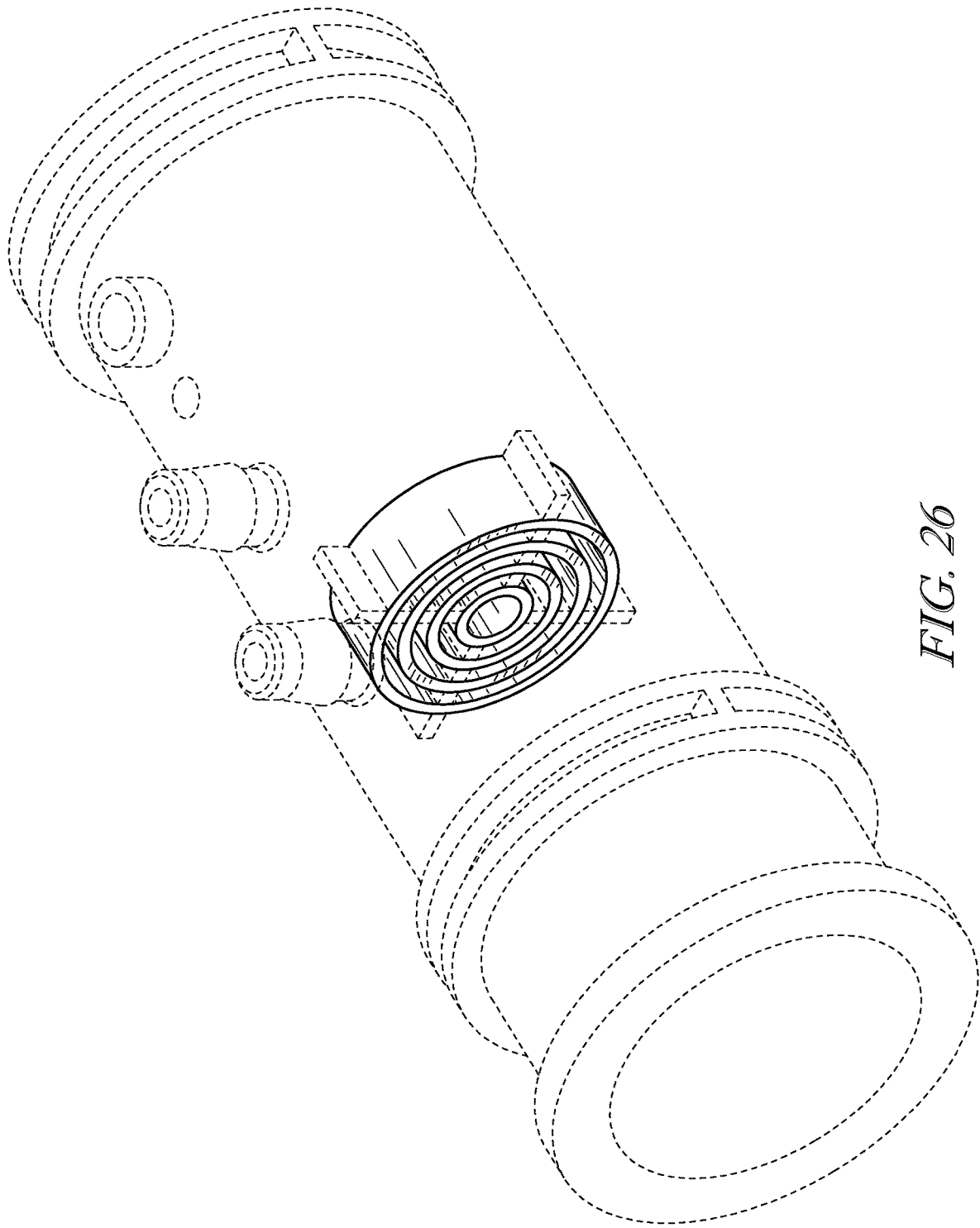
Figure 27:
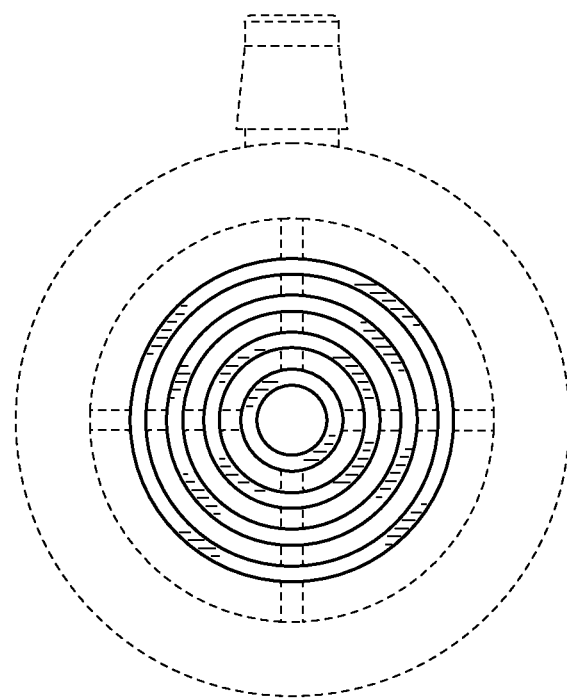
Figure 28:
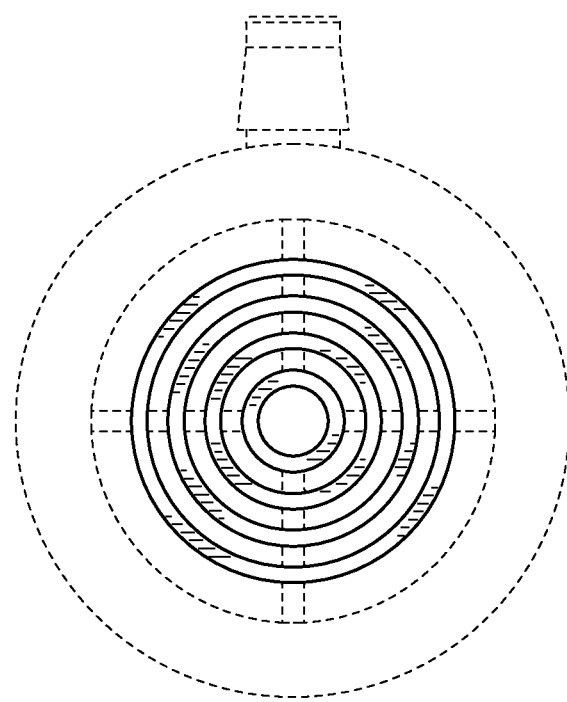
Figure 29:
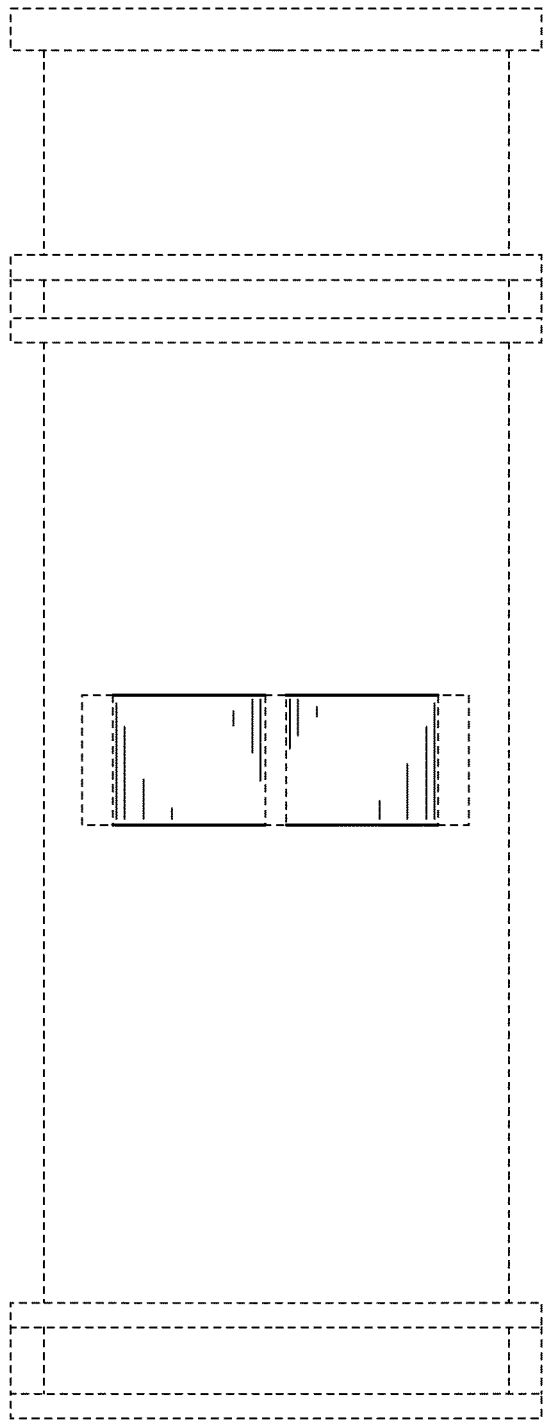
Figure 30:
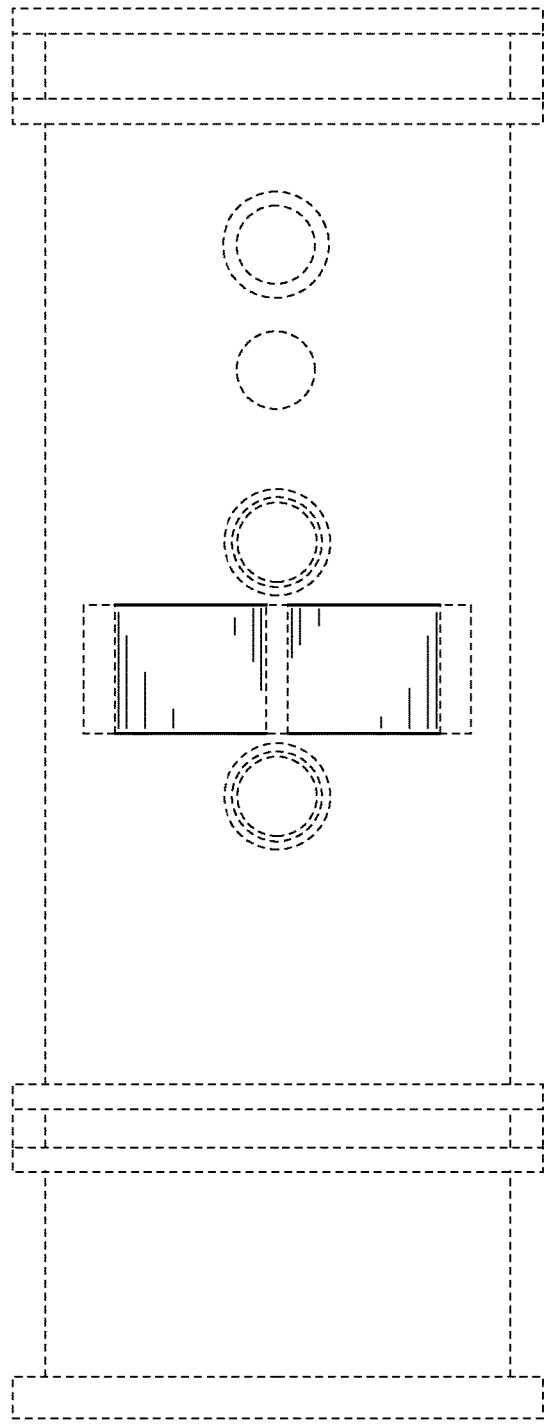
Figure 31:
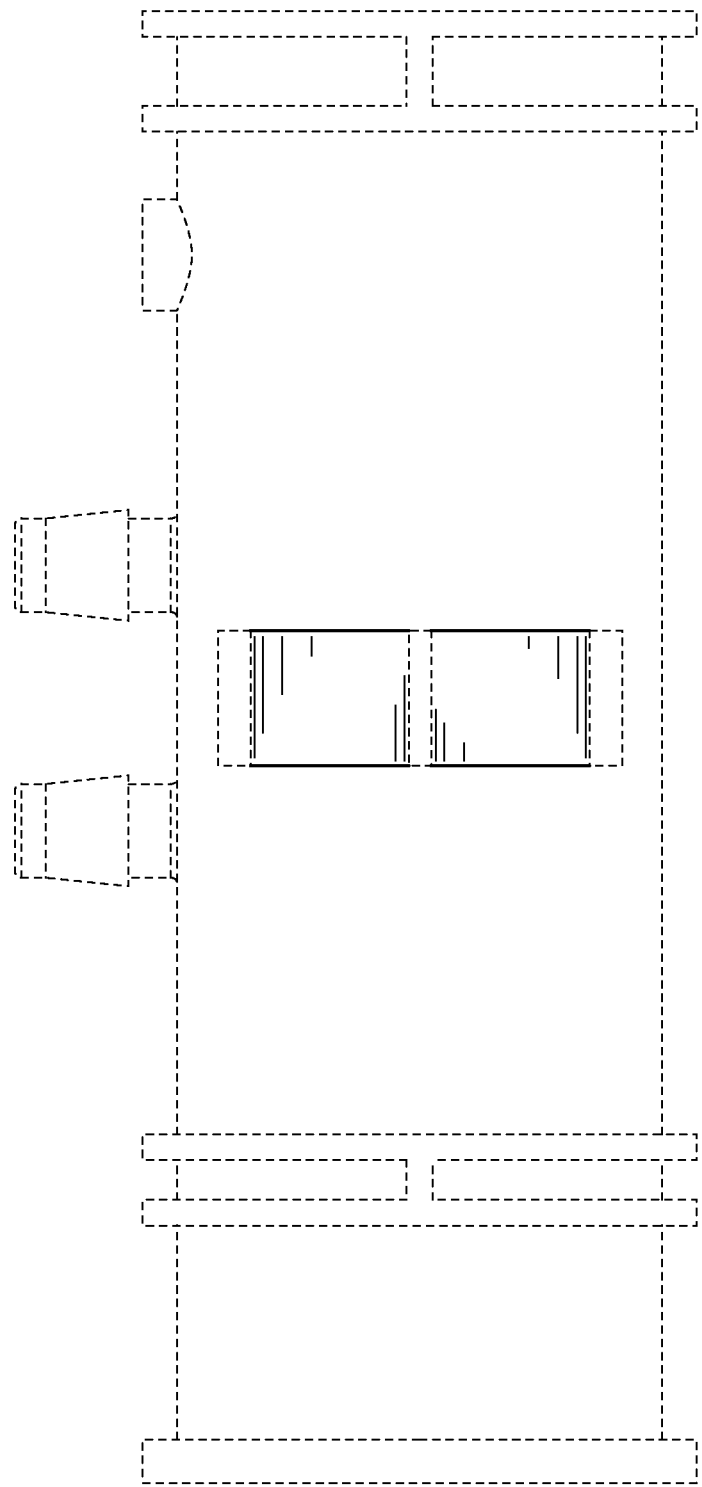
Figure 32:
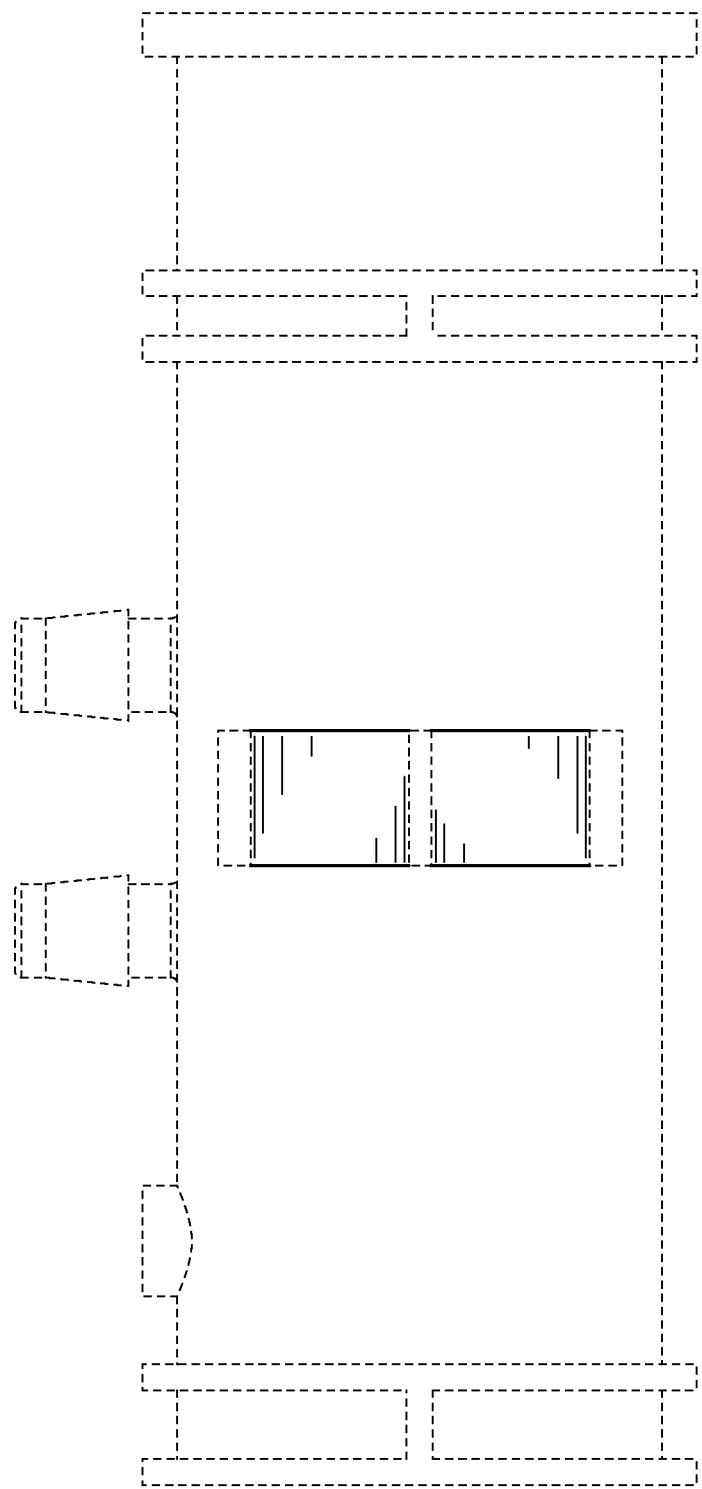
Figure 33:
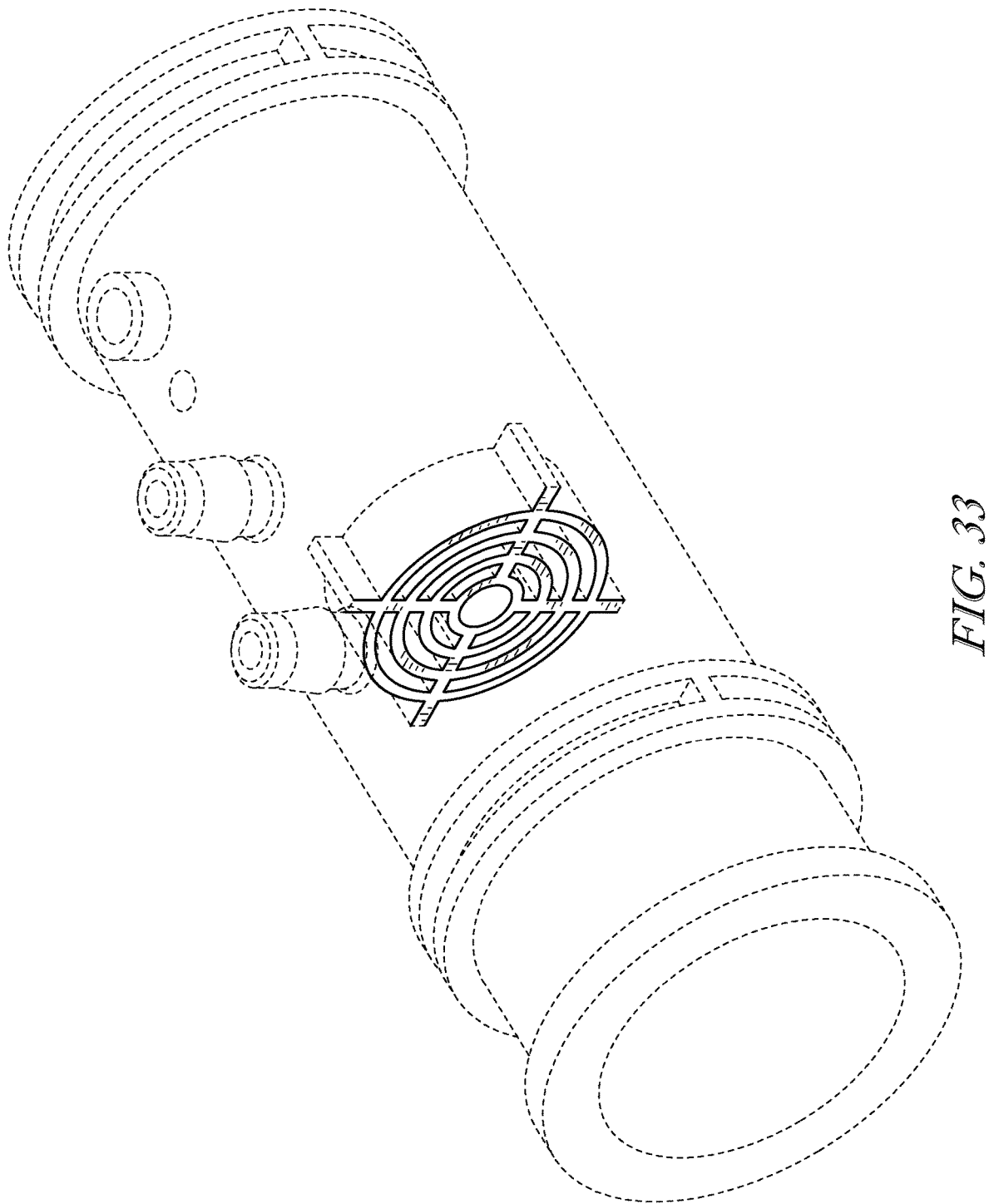
Figure 34:
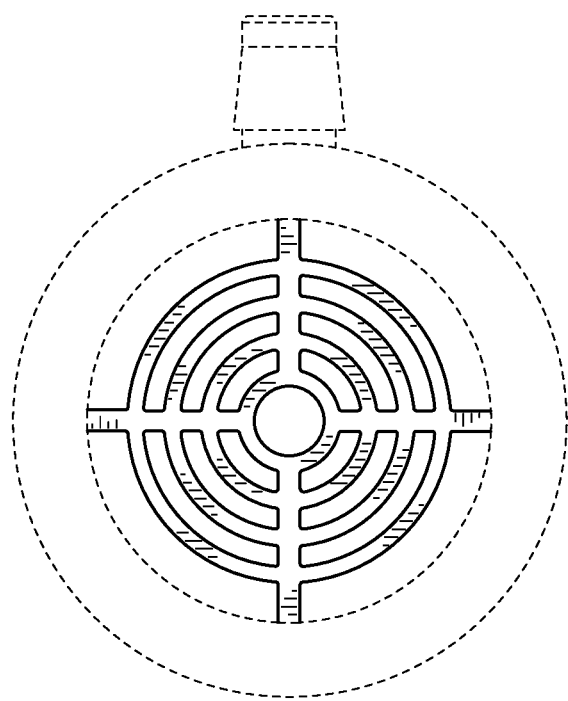
Figure 35:
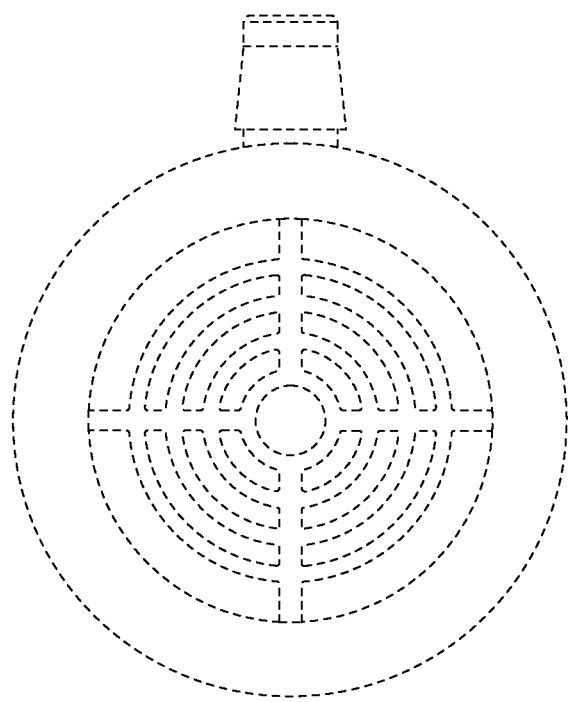
Figure 36:
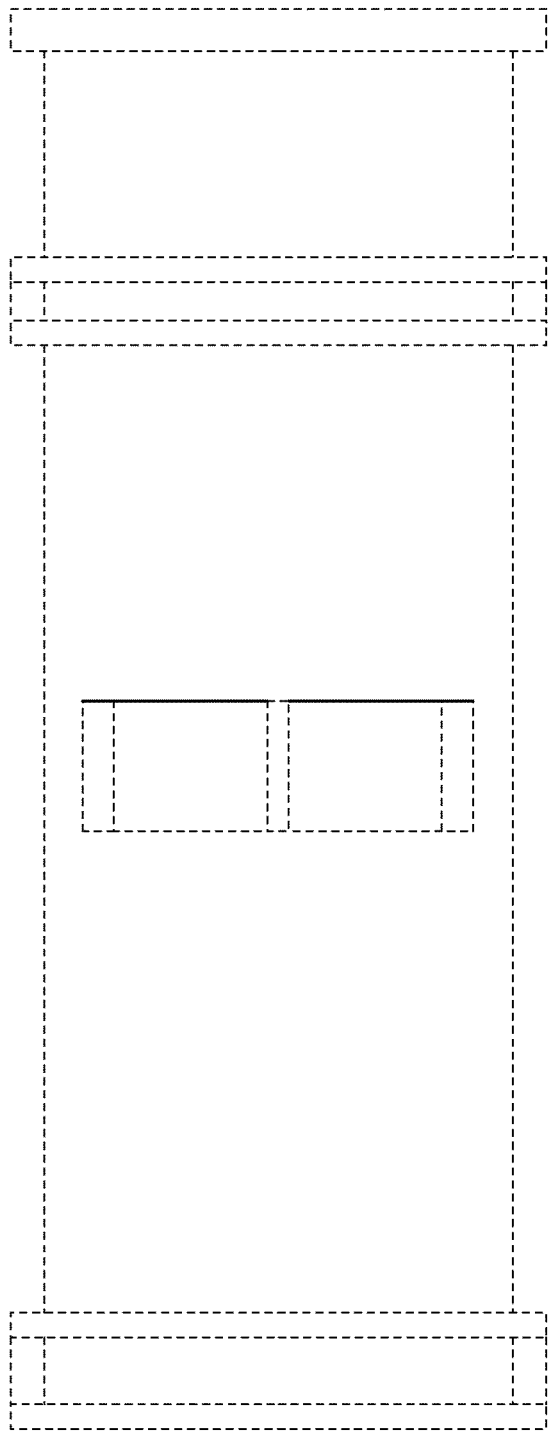
Figure 37:
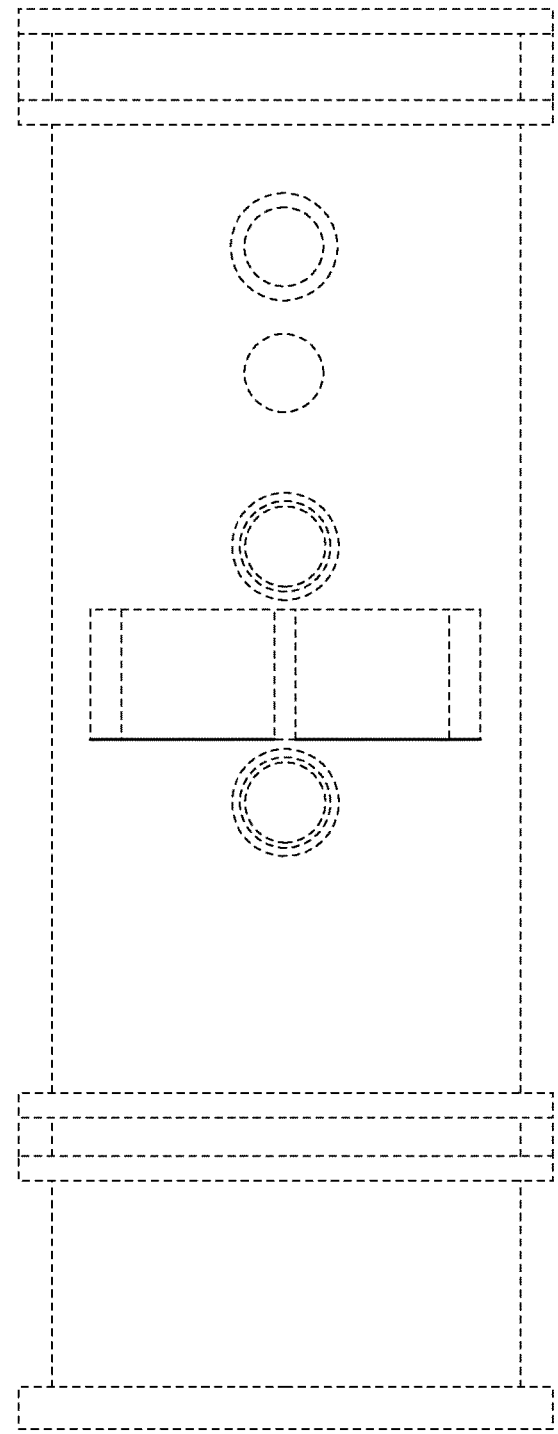
Figure 38:
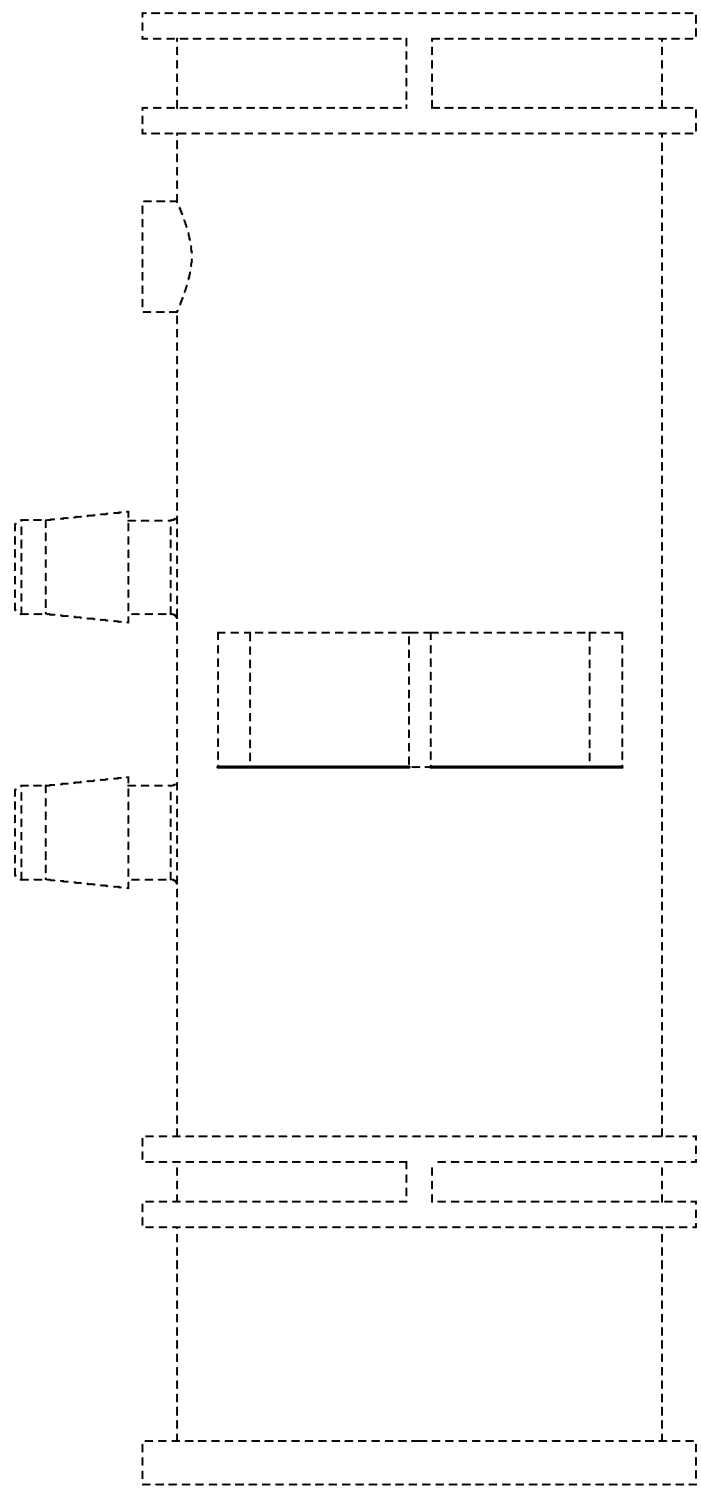
Figure 39:
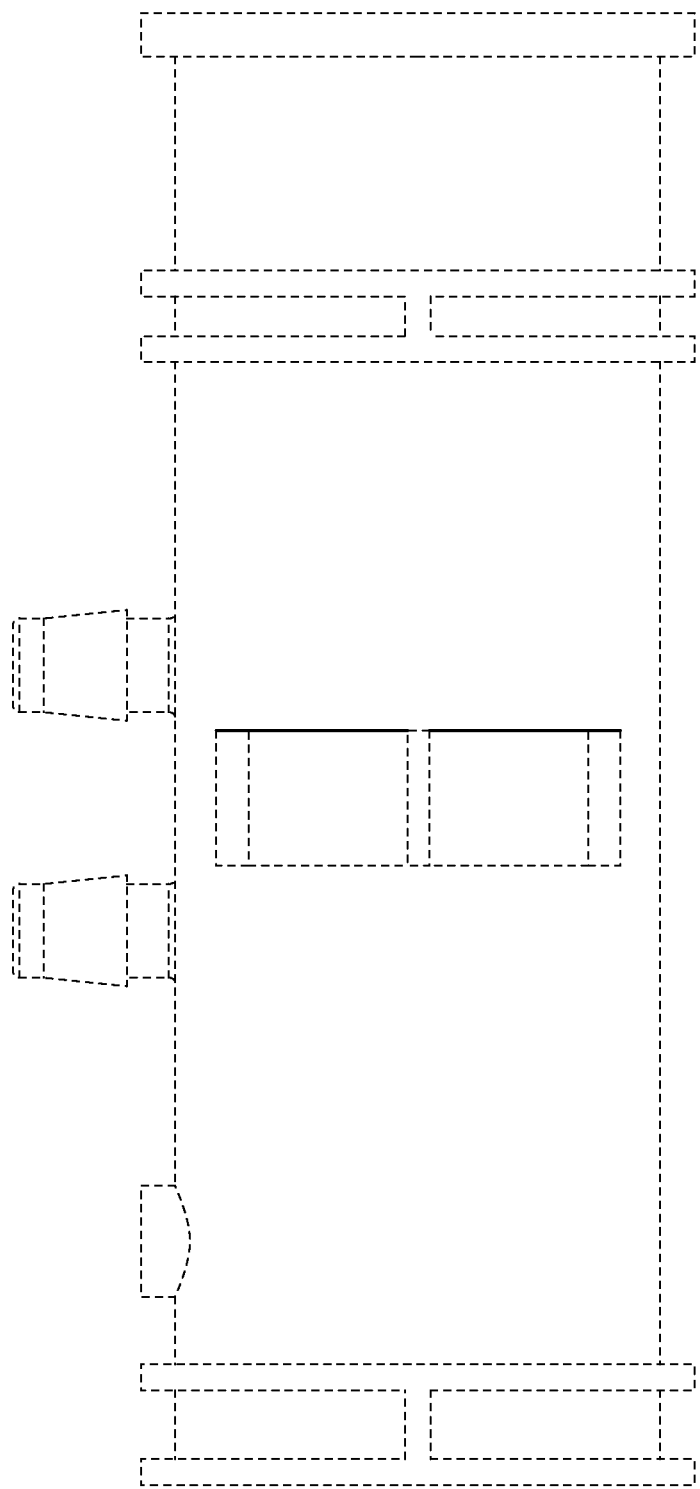
Figure 40:
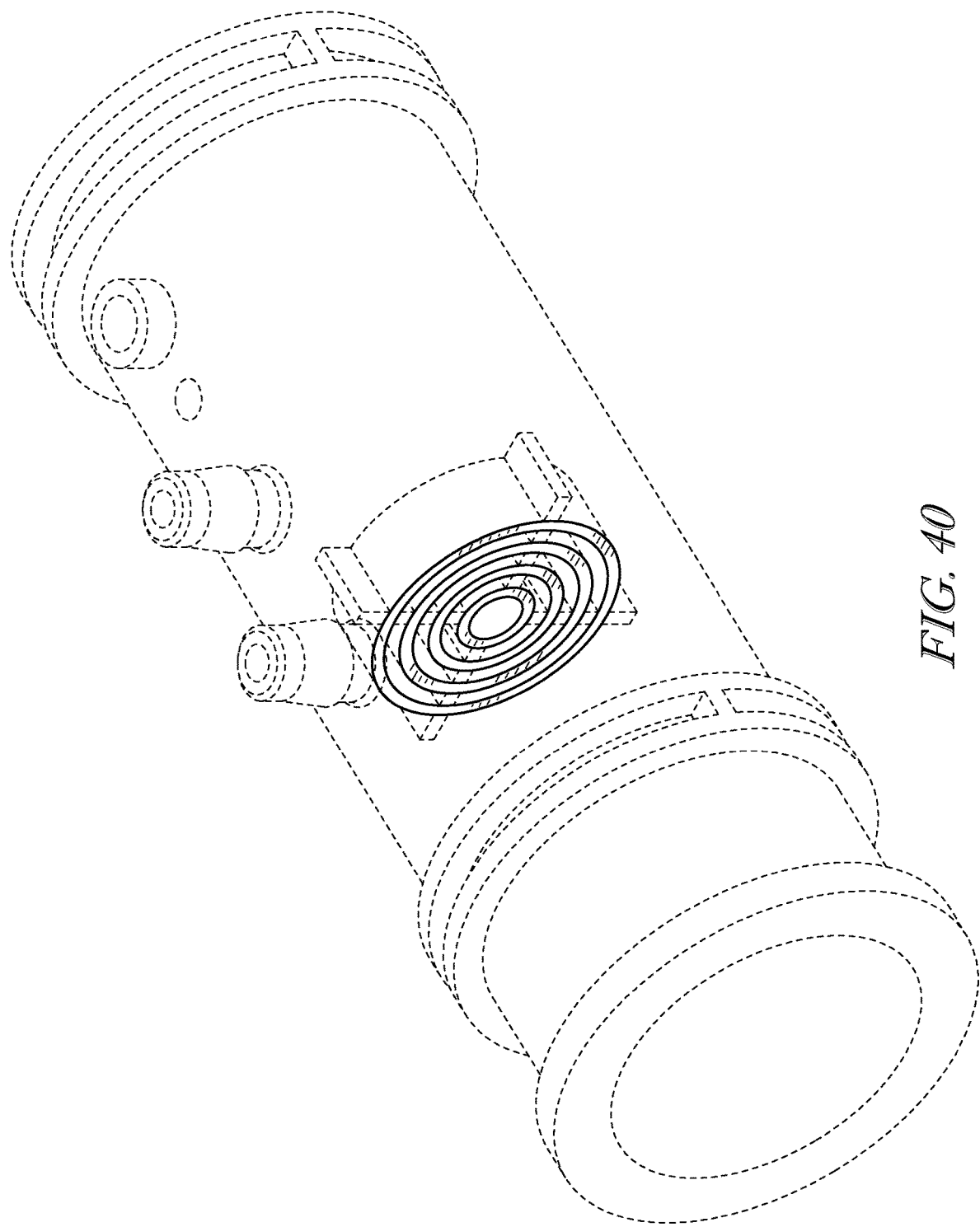
Figure 41:
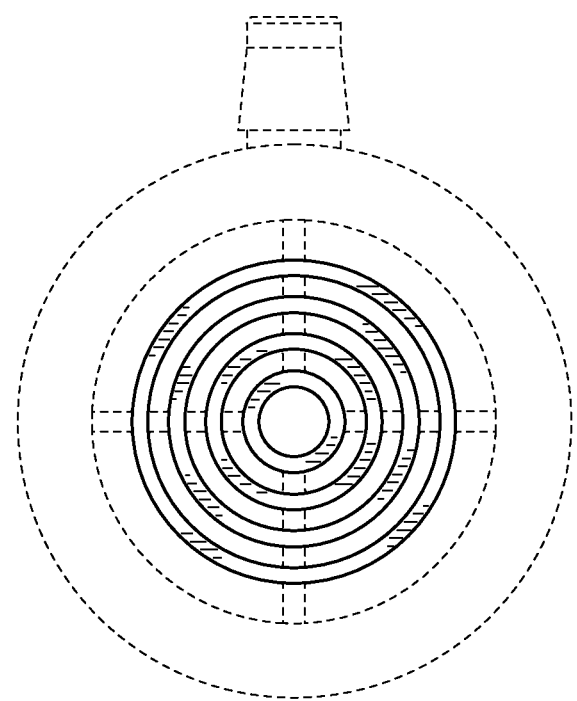
Figure 42:
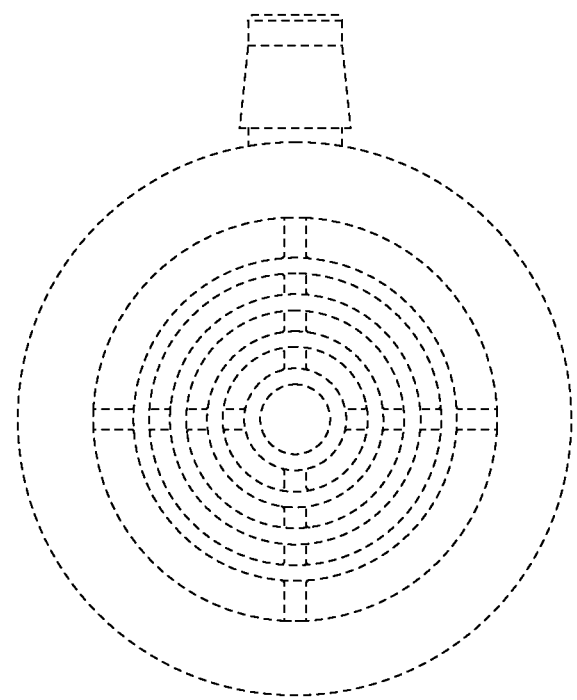
Figure 45:
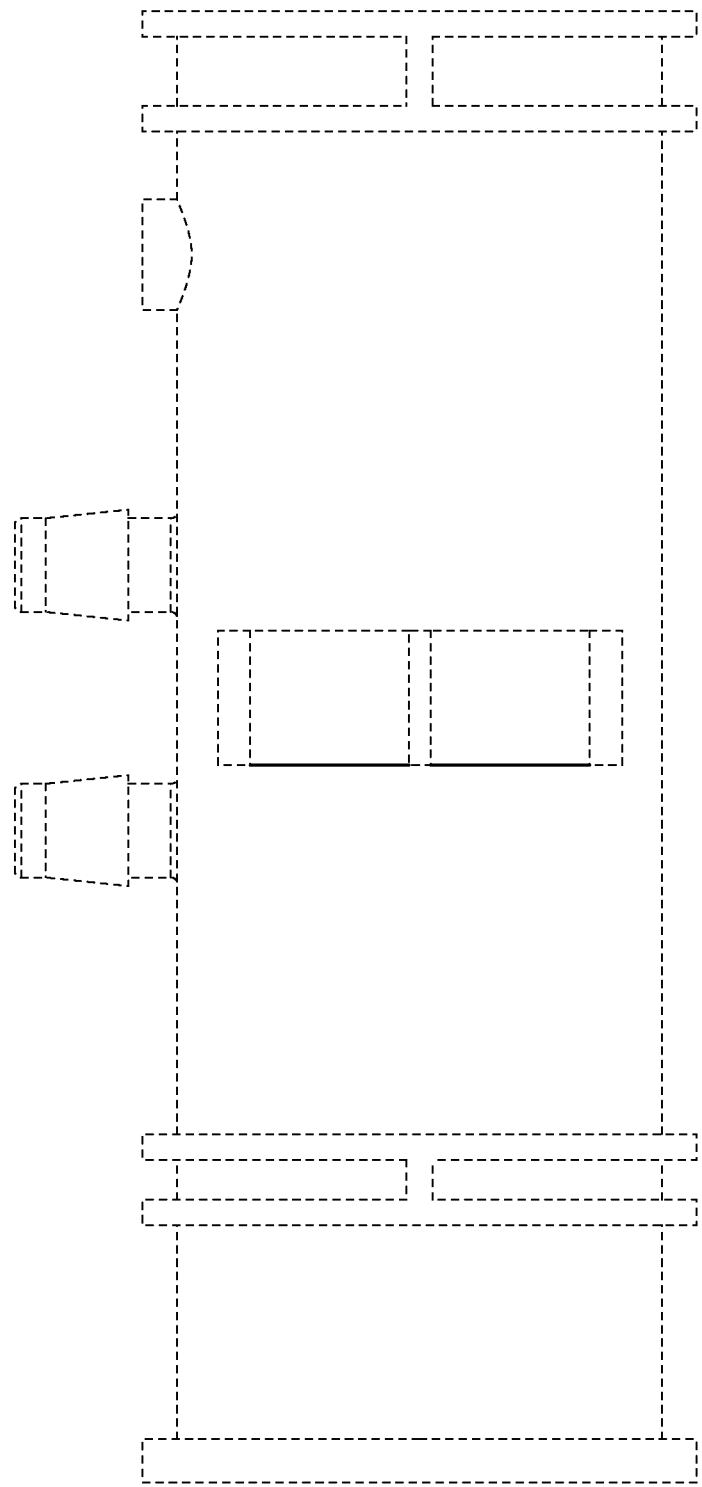
Figure 46:
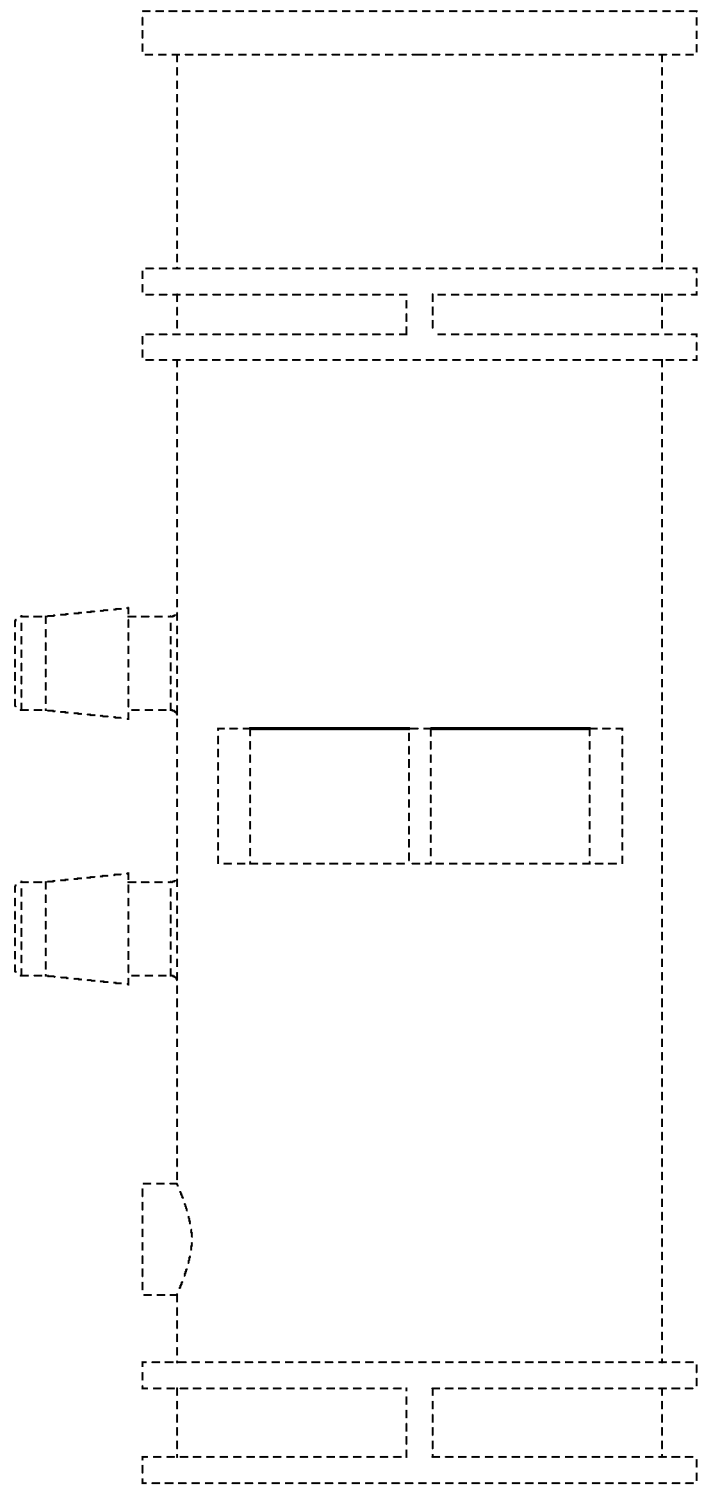

Referring to FIG. 18, housing 502 is configured to rotate with respect to handle 512 and adapter 510. For example, inlet 506 rotates with respect to handle outlet 516, and outlet 508 rotates with respect to patient interface, thereby enabling housing 502 to be positioned at any rotational position while maintaining a position of handle 512, hose 20, and adapter 510. A nebulizer port 520 is in flow communication with chamber 504. Nebulizer port 520 is positioned between inlet 506 and outlet 508. Nebulizer port 520 is configured to receive a nebulizer 522 therein to produce atomized medication. For example, the nebulizer 522 may be a jet nebulizer, an ultrasonic wave nebulizer, or a vibrating mesh nebulizer. By rotating housing 502, nebulizer port 520 may be positioned at any rotational position, thereby enabling a user to rotate nebulizer 522 to achieve a desired mixing of air and atomized medication within chamber 504. Nebulizer port 520 may include a removable cap (not shown) so that assembly 500 may be used without a nebulizer 522.

Although this disclosure refers to specific embodiments, it will be understood by those skilled in the art that various changes in form and detail may be made without departing from the subject matter set forth in the accompanying claims.

The invention claimed is:

1. A nebulizer assembly for a respiratory device comprising:
   a housing defining a chamber, the housing having an inlet in flow communication with the chamber and an outlet in flow communication with the chamber, the housing extending linearly along a central longitudinal axis of the housing between the inlet and the outlet, wherein the central longitudinal axis of the housing intersects an inlet plane formed by the inlet and an outlet plane formed by the outlet at an orthogonal angle relative to the central longitudinal axis, and wherein the inlet of the housing has a larger circumference than the outlet of the housing, the housing further having a nebulizer port configured to receive a nebulizer to discharge atomized medication into the chamber;
   a handle having an inlet and an outlet, the handle being curved smoothly to form an obtuse angle between the inlet and the outlet, wherein the outlet of the handle is coupled to the inlet of the housing, wherein the housing is circumferentially rotatable about the outlet of the handle so that the nebulizer is operable at all circumferential positions with respect to the outlet of the handle;
   a hose coupled to the inlet of the handle; and
   a patient interface coupled to the outlet of the housing, wherein air flows from the hose to the patient interface via the handle and the housing, the air mixing with the atomized medication within the chamber.

2. The nebulizer assembly of claim 1, wherein the outlet of the handle has a larger circumference than the inlet of the handle.

3. The nebulizer assembly of claim 1, wherein the housing has a substantially frusto-conical shape.

4. The nebulizer assembly of claim 1, further comprising at least one of a jet nebulizer, an ultrasonic wave nebulizer, or a vibrating mesh nebulizer coupled to the nebulizer port.

5. The nebulizer assembly of claim 1, wherein the patient interface comprises at least one of a mask or a mouthpiece.

6. The nebulizer assembly of claim 1, wherein the patient interface comprises an adapter that couples to at least one of a mask or a mouthpiece.

7. The nebulizer assembly of claim 1, wherein the hose is substantially non-linear to produce turbulent airflow through the hose.

8. The nebulizer assembly of claim 1, wherein the hose couples to a respiratory device.

9. The nebulizer assembly of claim 1, further comprising a nebulizer port cap to seal the nebulizer port when the nebulizer assembly is used without a nebulizer.

10. The nebulizer assembly of claim 1, further comprising a selector ring coupled to the inlet of the handle, wherein the selector ring rotates to release air from the handle.

11. A method of manufacturing a nebulizer assembly for a respiratory device, the method comprising:
   forming a housing defining a chamber,
   forming an inlet in flow communication with the chamber and an outlet in flow communication with the chamber, the housing extending linearly along a central longitudinal axis of the housing between the inlet and the outlet, wherein the central longitudinal axis of the housing intersects an inlet plane formed by the inlet and an outlet plane formed by the outlet at an orthogonal angle relative to the central longitudinal axis, and wherein the inlet of the housing has a larger circumference than the outlet of the housing,
   extending a nebulizer port from the chamber to receive a nebulizer that discharges atomized medication into the chamber;
   coupling an outlet of a handle to the inlet of the housing so that the housing is circumferentially rotatable about the outlet of the handle so that the nebulizer is operable at all circumferential positions with respect to the outlet of the handle, wherein the handle is curved smoothly to form an obtuse angle between an inlet of the handle and the outlet of the handle.

12. The method of claim 11, further comprising forming the inlet of the housing to couple to a hose.

13. The method of claim 12, further comprising forming the outlet of the handle to couple to a patient interface.

14. The method of claim 13, further comprising forming the chamber so that air from the hose mixes with the atomized medication within the chamber.

15. The method of claim 11, further comprising forming the outlet of the handle with a larger circumference than an inlet of the handle.

16. The method of claim 11, further comprising forming the housing with a substantially frusto-conical shape.

17. The method of claim 11, further comprising forming a nebulizer port cap to seal the nebulizer port when the nebulizer assembly is used without a nebulizer.

18. The method of claim 11, further comprising coupling a selector ring to the inlet of the handle, wherein the selector ring rotates to release air from the handle.

* * * * *